(12) United States Patent
Gephart

(10) Patent No.: US 11,857,231 B2
(45) Date of Patent: Jan. 2, 2024

(54) BONE COMPRESSION DEVICE AND METHOD

(71) Applicant: Pioneer Surgical Technology, Inc., Alachua, FL (US)

(72) Inventor: Matthew P. Gephart, Marquette, MI (US)

(73) Assignee: Pioneer Surgical Technology, Inc., Alachua, FL (US)

( * ) Notice: Subject to any disclaimer, the term of this patent is extended or adjusted under 35 U.S.C. 154(b) by 340 days.

(21) Appl. No.: 17/158,628

(22) Filed: Jan. 26, 2021

(65) Prior Publication Data

US 2021/0220029 A1    Jul. 22, 2021

Related U.S. Application Data

(63) Continuation of application No. 16/164,899, filed on Oct. 19, 2018, now Pat. No. 10,932,833, which is a
(Continued)

(51) Int. Cl.
| | |
|---|---|
| *A61B 17/80* | (2006.01) |
| *A61B 17/86* | (2006.01) |
| *A61B 17/17* | (2006.01) |
| *A61B 17/88* | (2006.01) |
| *A61B 17/064* | (2006.01) |
| *A61B 17/00* | (2006.01) |

(52) U.S. Cl.
CPC ........ *A61B 17/808* (2013.01); *A61B 17/1728* (2013.01); *A61B 17/8004* (2013.01); *A61B 17/8085* (2013.01); *A61B 17/8645* (2013.01); *A61B 17/8863* (2013.01); *A61B 17/0642* (2013.01); *A61B 2017/00867* (2013.01)

(58) Field of Classification Search
CPC .......... A61B 17/808; A61B 2017/0645; A61B 17/8085; A61B 17/8004
See application file for complete search history.

(56) References Cited

U.S. PATENT DOCUMENTS

| | | | |
|---|---|---|---|
| 2,580,821 | A | 1/1952 | Nicola |
| 3,710,789 | A | 1/1973 | Ersek |

(Continued)

FOREIGN PATENT DOCUMENTS

| | | |
|---|---|---|
| DE | 3808937 | 10/1989 |
| WO | 0062693 | 10/2000 |
| WO | 2012162733 | 12/2012 |

OTHER PUBLICATIONS

U.S. Appl. No. 62/692,464, filed Jun. 29, 2018, Gephart Matthew P.
(Continued)

*Primary Examiner* — Andrew Yang
(74) *Attorney, Agent, or Firm* — Fitch, Even, Tabin & Flannery LLP

(57) ABSTRACT

In one form, a bone compression device is provided having a shape-retentive bone plate with an initial, unflexed configuration and a flexed configuration. The bone plate may be shifted to the flexed configuration and secured to bones using bone screws of the bone compression device. Once the bone plate has been secured to the bones, the bone plate returns toward its unflexed configuration which compresses the bones.

25 Claims, 30 Drawing Sheets

Related U.S. Application Data continuation of application No. 15/058,695, filed on Mar. 2, 2016, now Pat. No. 10,123,831.

(60) Provisional application No. 62/127,609, filed on Mar. 3, 2015.

(56) References Cited

U.S. PATENT DOCUMENTS

| | | |
|---|---|---|
| 3,900,025 A | 8/1975 | Barnes, Jr. |
| 3,939,828 A | 2/1976 | Mohr et al. |
| 4,364,382 A | 12/1982 | Mennen |
| 5,026,390 A | 6/1991 | Brown |
| 5,281,226 A | 1/1994 | Davydov et al. |
| 5,423,816 A | 6/1995 | Lin |
| 5,423,826 A * | 6/1995 | Coates ............ A61B 17/1757 606/291 |
| 5,458,642 A | 10/1995 | Beer et al. |
| 5,620,443 A | 4/1997 | Gertzbein et al. |
| 5,713,900 A | 2/1998 | Benzel et al. |
| 5,735,853 A | 4/1998 | Olerud |
| 5,766,218 A | 6/1998 | Arnott |
| 5,785,713 A | 7/1998 | Jobe |
| 6,117,135 A | 9/2000 | Schlaepfer |
| 6,136,002 A | 10/2000 | Shih et al. |
| 6,342,055 B1 | 1/2002 | Eisermann et al. |
| 6,645,207 B2 | 11/2003 | Dixon et al. |
| 6,695,846 B2 | 2/2004 | Richelsoph et al. |
| 6,719,793 B2 | 4/2004 | McGee |
| 6,783,531 B2 | 8/2004 | Allen |
| 6,986,771 B2 | 1/2006 | Paul et al. |
| 7,008,427 B2 | 3/2006 | Sevrain |
| 7,115,129 B2 * | 10/2006 | Heggeness ............ A61B 17/808 606/279 |
| 7,591,840 B2 | 9/2009 | Suddaby |
| 7,749,256 B2 | 7/2010 | Farris et al. |
| 7,763,056 B2 | 7/2010 | Dalton |
| 7,833,256 B2 | 11/2010 | Biedermann et al. |
| 7,857,836 B2 | 12/2010 | Huebner et al. |
| 7,914,561 B2 | 3/2011 | Konieczynski et al. |
| 7,931,679 B2 | 4/2011 | Heggeness |
| 7,972,366 B2 | 7/2011 | Richelsoph et al. |
| 7,993,380 B2 | 8/2011 | Hawkes |
| 8,043,346 B2 | 10/2011 | Markworth |
| 8,216,285 B2 | 7/2012 | Markworth |
| 8,226,693 B2 | 7/2012 | Reimels et al. |
| 8,257,404 B2 | 9/2012 | Hack |
| 8,262,711 B2 | 9/2012 | Hess |
| 8,500,737 B2 | 8/2013 | Richelsoph et al. |
| 8,574,270 B2 | 11/2013 | Hess et al. |
| 8,585,742 B2 | 11/2013 | Windolf |
| 8,623,019 B2 | 1/2014 | Perrow et al. |
| 8,728,127 B2 | 5/2014 | Stewart |
| 8,747,441 B2 | 6/2014 | Konieczynski et al. |
| 8,758,347 B2 | 6/2014 | Weiner et al. |
| 8,790,379 B2 | 7/2014 | Bottlang et al. |
| 8,814,915 B2 | 8/2014 | Hess et al. |
| 8,882,812 B2 | 11/2014 | Hess et al. |
| 8,882,815 B2 | 11/2014 | Bottlang et al. |
| 8,974,504 B2 | 3/2015 | Hess et al. |
| 8,992,583 B2 | 3/2015 | Bottlang et al. |
| 9,005,255 B2 | 4/2015 | Lewis et al. |
| 9,005,257 B2 | 4/2015 | Sun |
| 9,033,988 B2 | 5/2015 | Gephart et al. |
| 9,095,388 B2 | 8/2015 | Hess et al. |
| 9,198,769 B2 | 12/2015 | Perrow et al. |
| 9,295,503 B2 | 3/2016 | Frigg et al. |
| 9,295,508 B2 | 3/2016 | Bottlang et al. |
| 9,351,774 B2 | 5/2016 | Konieczynski et al. |
| 9,381,046 B2 | 7/2016 | Perrow et al. |
| 9,408,647 B2 * | 8/2016 | Cheney ............ A61B 17/1728 |
| 9,498,259 B2 | 11/2016 | Dirisio et al. |
| 9,510,879 B2 | 12/2016 | Bottlang et al. |
| 9,579,135 B2 | 2/2017 | Cook et al. |
| 9,700,361 B2 | 7/2017 | Bottlang et al. |
| 9,763,713 B2 | 9/2017 | Bottlang et al. |
| 9,788,863 B2 | 10/2017 | Juchno et al. |
| 9,788,873 B2 | 10/2017 | Bottlang et al. |
| 9,855,082 B2 | 1/2018 | Hulliger et al. |
| 9,883,897 B2 | 2/2018 | Taber |
| 9,924,987 B2 | 3/2018 | Cheney |
| 10,022,168 B2 | 7/2018 | Bottlang et al. |
| 10,070,905 B2 | 9/2018 | Bottlang et al. |
| 10,092,336 B2 | 10/2018 | Hess et al. |
| 10,123,831 B2 | 11/2018 | Gephart |
| 10,159,514 B2 | 12/2018 | Perrow et al. |
| 10,226,291 B2 | 3/2019 | Perrow et al. |
| 10,932,833 B2 | 3/2021 | Gephart |
| 2004/0039388 A1 | 2/2004 | Biedermann et al. |
| 2004/0087955 A1 | 5/2004 | Bordi |
| 2004/0116931 A1 | 6/2004 | Carlson |
| 2004/0147928 A1 | 7/2004 | Landry et al. |
| 2005/0004573 A1 | 1/2005 | Abdou |
| 2005/0043732 A1 | 2/2005 | Dalton |
| 2005/0203513 A1 | 9/2005 | Jahng et al. |
| 2006/0167457 A1 | 7/2006 | Suddaby |
| 2007/0055251 A1 | 3/2007 | Huebner et al. |
| 2007/0213727 A1 | 9/2007 | Bottlang et al. |
| 2008/0147124 A1 | 6/2008 | Haidukewych et al. |
| 2008/0269753 A1 | 10/2008 | Cannestra |
| 2009/0069812 A1 | 3/2009 | Gillard et al. |
| 2010/0036430 A1 | 2/2010 | Hartdegen et al. |
| 2010/0063505 A1 | 3/2010 | Frigg et al. |
| 2011/0106182 A1 | 5/2011 | Reisberg |
| 2011/0295324 A1 | 12/2011 | Donley et al. |
| 2012/0296440 A1 | 11/2012 | Choux et al. |
| 2013/0090695 A1 | 4/2013 | Bernstein et al. |
| 2013/0190762 A1 | 7/2013 | Frankle et al. |
| 2014/0039630 A1 | 2/2014 | Peyrot et al. |
| 2014/0188178 A1 | 7/2014 | Juchno et al. |
| 2015/0157374 A1 | 6/2015 | Gephart et al. |
| 2015/0230843 A1 | 8/2015 | Palmer et al. |
| 2015/0238238 A1 | 8/2015 | Cheney |
| 2015/0289918 A1 | 10/2015 | Burckhardt et al. |
| 2015/0313656 A1 | 11/2015 | Hulliger |
| 2016/0074082 A1 | 3/2016 | Cremer et al. |
| 2016/0157905 A1 | 6/2016 | Arellano et al. |
| 2016/0166296 A9 | 6/2016 | Juchno et al. |
| 2016/0256203 A1 | 9/2016 | Gephart |
| 2016/0270831 A1 | 9/2016 | Perrow et al. |
| 2017/0360487 A1 | 12/2017 | Moseley et al. |
| 2018/0000520 A1 | 1/2018 | Juchno et al. |
| 2018/0036048 A1 | 2/2018 | Bottlang et al. |
| 2018/0070997 A1 | 3/2018 | Bottlang et al. |
| 2018/0078296 A1 | 3/2018 | Hulliger et al. |
| 2019/0046247 A1 | 2/2019 | Gephart |
| 2019/0175234 A1 | 6/2019 | Perrow et al. |
| 2020/0000501 A1 | 1/2020 | Gephart |

OTHER PUBLICATIONS

Charlotte Claw Compression Plate, Wright Medical Technology, Inc., 2 pages, 2015.

F. Paris, V. Tarazona, E. Blasco, A. Canto, M. Casillas, J. Pastor, M. Paris, and R. Montero, Surgical stabilization of traumatic flail chest, Thorax (1975), 30, pp. 521-527.

Johnson Matthey Medical Components, How Does Nitinol Work? All About Nitinol Shape Memory and Superelasticity, retrieved on Jun. 21, 2018; http://jmmedical.com/resources/122/How-Does-Nitinol-Work%3F-All-About-Nitinol-Shape-Memory-and-Superelasticity.html; 2 pages.

U.S. Appl. No. 17/211,489, filed Mar. 24, 2021 (43 pages).

* cited by examiner

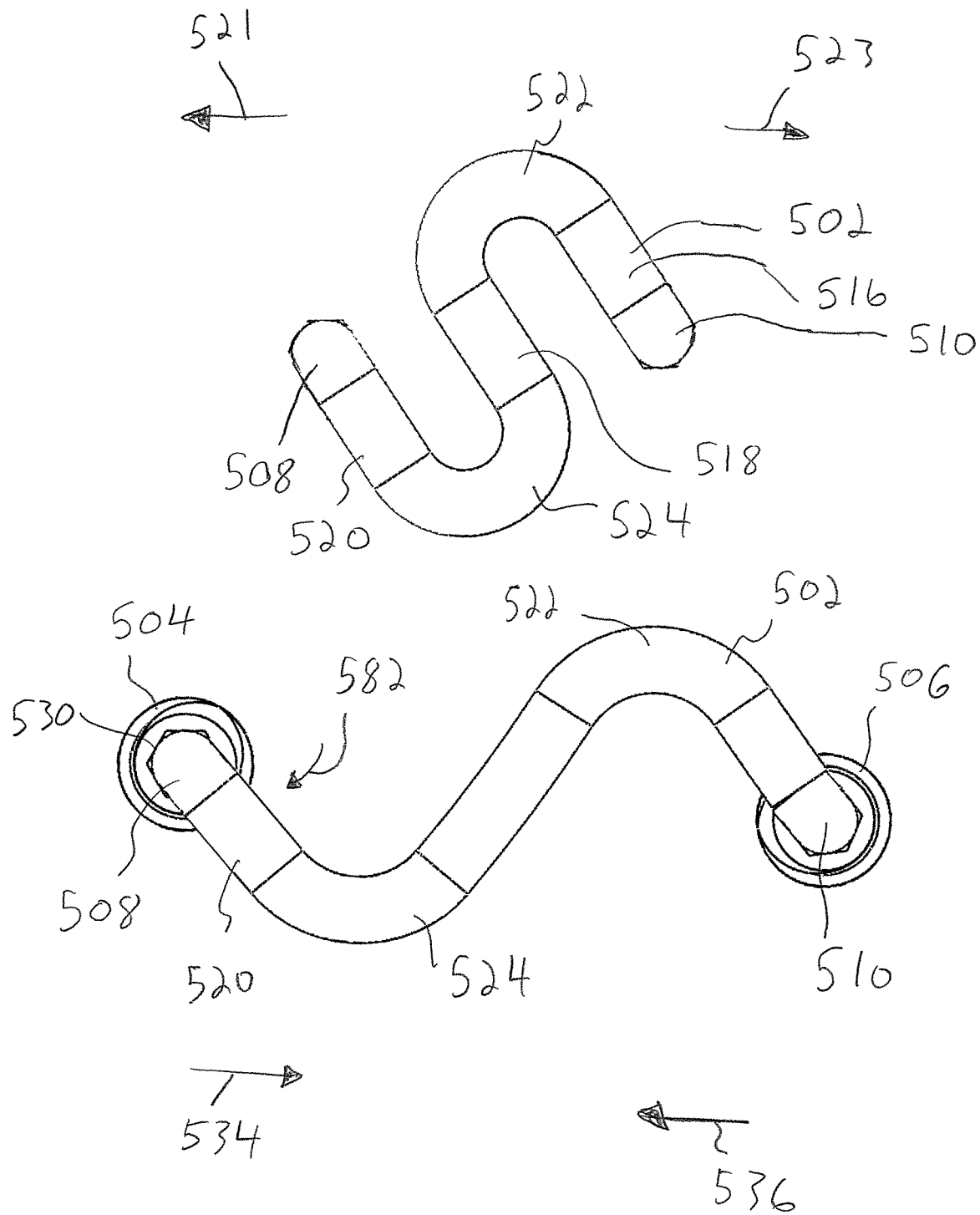

BONE COMPRESSION DEVICE AND METHOD

CROSS-REFERENCE TO RELATED APPLICATIONS

This application is a continuation of U.S. patent application Ser. No. 16/164,899, filed Oct. 19, 2018, now U.S. Pat. No. 10,932,833, granted Mar. 2, 2021, which is a continuation of U.S. patent application Ser. No. 15/058,695, filed Mar. 2, 2016, now U.S. Pat. No. 10,123,831, granted Nov. 13, 2018, which claims the benefit of U.S. Provisional Patent Application No. 62/127,609, filed Mar. 3, 2015, which are all hereby incorporated by reference in their entireties.

FIELD OF THE INVENTION

The invention relates to the stabilization of bones and, more particularly, to devices for compressing bones together to encourage bone growth.

BACKGROUND

Nitinol staples are often used to stabilize bones in orthopedic podiatry, hand, and wrist surgeries. As used herein, the term "bone" is intended to refer to whole bones, bone fragments, and other portions of the skeleton. Nitinol staples may be used to compress a pair of bones separated by a cut or break to encourage healing. Nitinol staples may also be used to compress a pair of bones on opposite sides of an implant to encourage fusion of the bones and implant construct.

A nitinol staple may be implanted by first drilling holes for legs of the staple in the bones sought to be stabilized. The legs of the staple are splayed apart, which elastically deforms the staple, and are inserted into the holes. The resilient properties of the nitinol staple tend to draw the legs back together which compresses the bones. The compressive force applied by the staple encourages bone growth between the bones.

A nitinol staple provides a limited amount of compression which is in acceptable in some applications. In other applications, however, a greater amount of compression or increased stability is desired such that two staples are implanted in the bones. Specifically, one staple is implanted in one side of the bones and the other staple is implanted in an opposite side of the bones. Implanting two staples on opposite sides of the bones may complicate the surgical procedure. Further, in some applications, a greater amount of compression and/or increased stability is desired but the surrounding anatomy may inhibit the use of two staples on opposite sides of the bones.

Another problem with the use of nitinol staples is that a large number of staples are provided in a surgical kit. For example, a surgical kit may include staples having different staple bridge lengths to position the legs of the staples different distances apart. For each staple bridge length, the surgical kit would also include staples with different leg lengths. Providing both a range of staple bridge lengths and staple leg lengths significantly increases the number of staples required in the kit.

BRIEF DESCRIPTION OF THE DRAWINGS

FIG. 33 is a top plan view of the resilient body of FIG. 32 in an unflexed configuration;

FIG. 34 is a view similar to FIG. 33 showing end portions of the resilient body moved apart from one another to reconfigure the resilient body to a flexed configuration;

DETAILED DESCRIPTION

Figure 1:
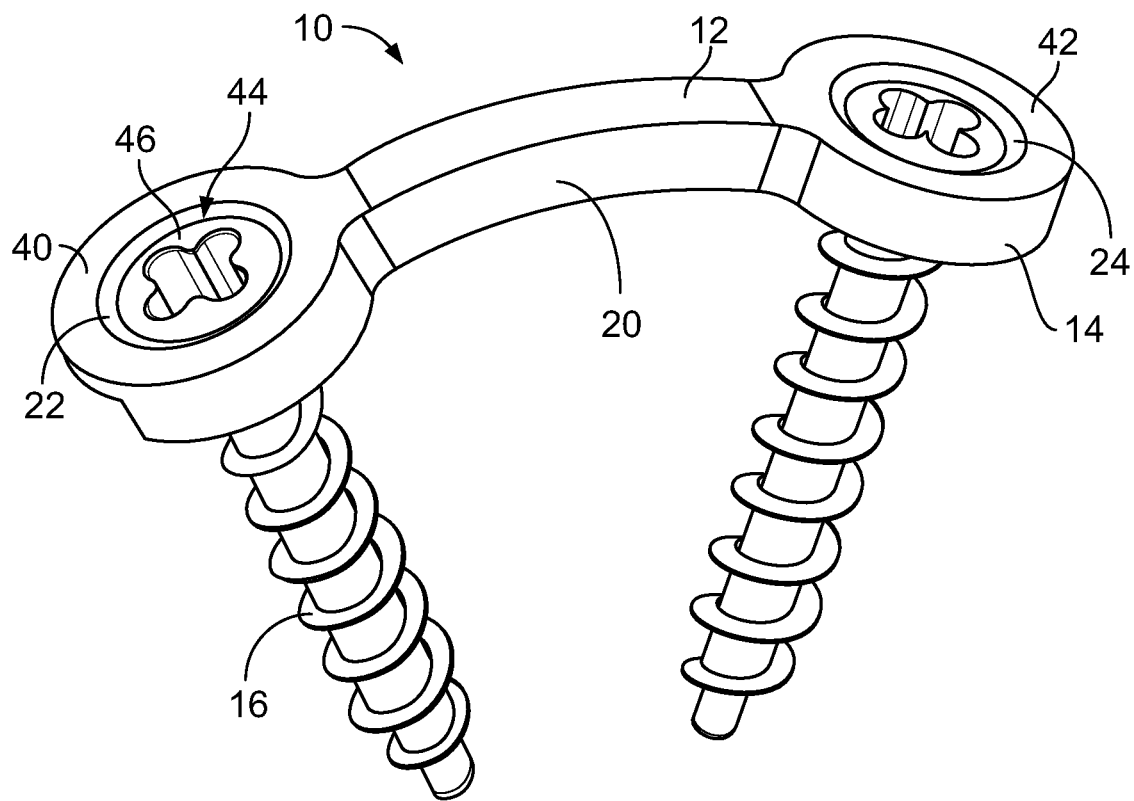
FIG. 1 is a perspective view of a bone compression device having a bone plate and bone screws for securing the bone plate to bones.

In FIG. 1, a bone compression device 10 is provided having a bone plate 12 with a body 14 for being secured to bones with bone anchors, such as bone screws 16. The bone plate 12 is made entirely or partially of a shape-retentive material that permits elastic deformation of the bone plate 12 and resiliently biases the bone screws 16 and bones connected thereto together once the bone plate 12 has been implanted on the bones. In one form, the bone plate 12 is made of nitinol having superelastic properties that permits the bone plate 12 to deform elastically as the bone plate 12 is flexed during implantation of the bone plate 12, as discussed in greater detail below. Once the bone plate 12 is implanted in a flexed configuration thereof, the bone plate 12 acts as a spring and applies constant compression to the bones until the elastically deformed bone plate 12 returns toward its initial, unflexed configuration. This is an improvement over some prior compression bone plates that are plastically deformed to compress bones. In these bone plates, there may be spring back within the bone plate after implantation of the bone plate which reduces the compression applied to the bones. As another example, the bone plate 12 may be made from a shape memory material, such as shape memory nitinol, which would compress the bones by changing shape in situ from a flexed configuration to an unflexed configuration in response to the internal temperature of the patient.

Figure 2:
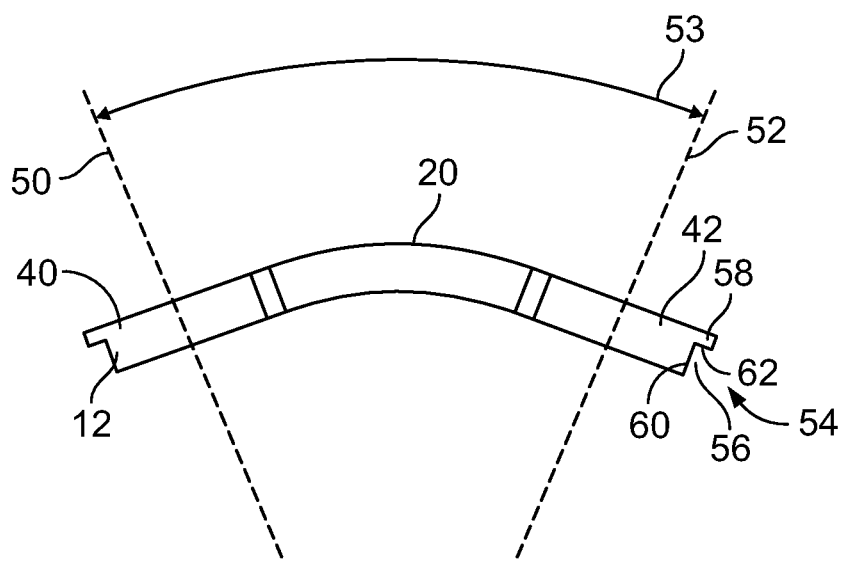
FIG. 2 is a side elevational view of the bone plate of FIG. 1 showing the bone plate in an initial, unflexed configuration with an intermediate portion of the bone plate having a curved shape.
Figure 7:
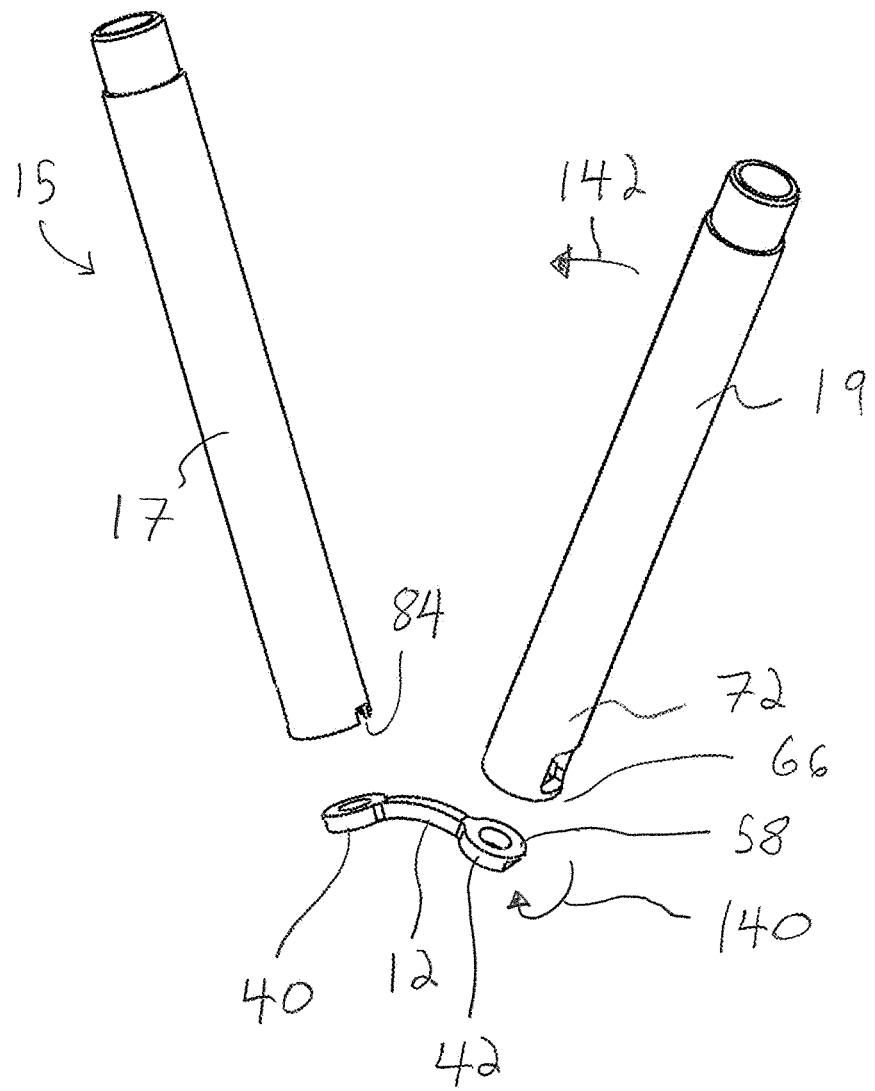
FIG. 7 is a schematic view showing the manipulators positioned above the lobes of the bone plate of FIG. 1 for connection therewith.
Figure 11:
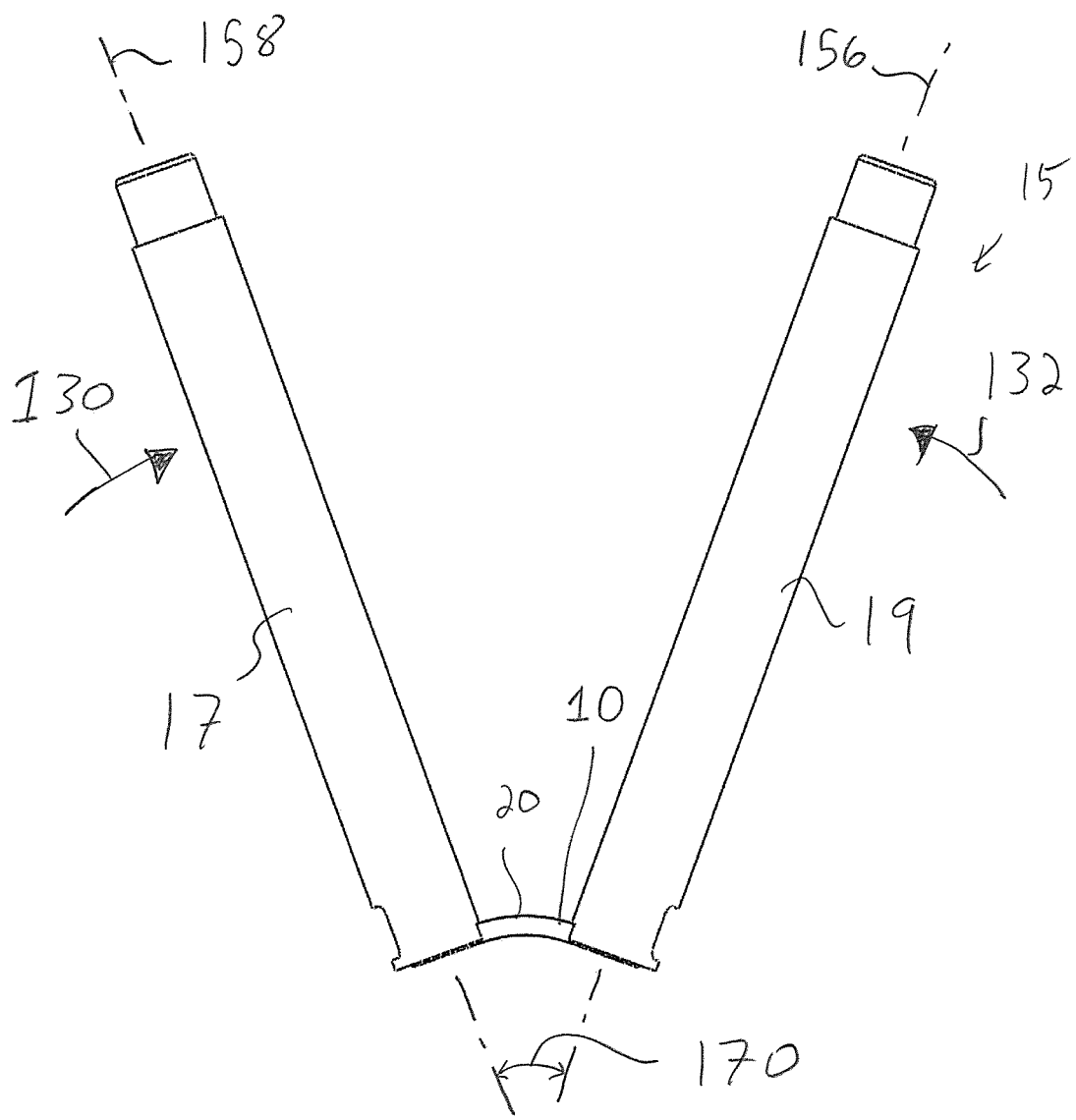
FIG. 11 is a side elevational view of the manipulators and bone plate of FIG. 10 showing center lines of the manipulator cannulas oriented at an angle relative to one each other.
Figure 12:
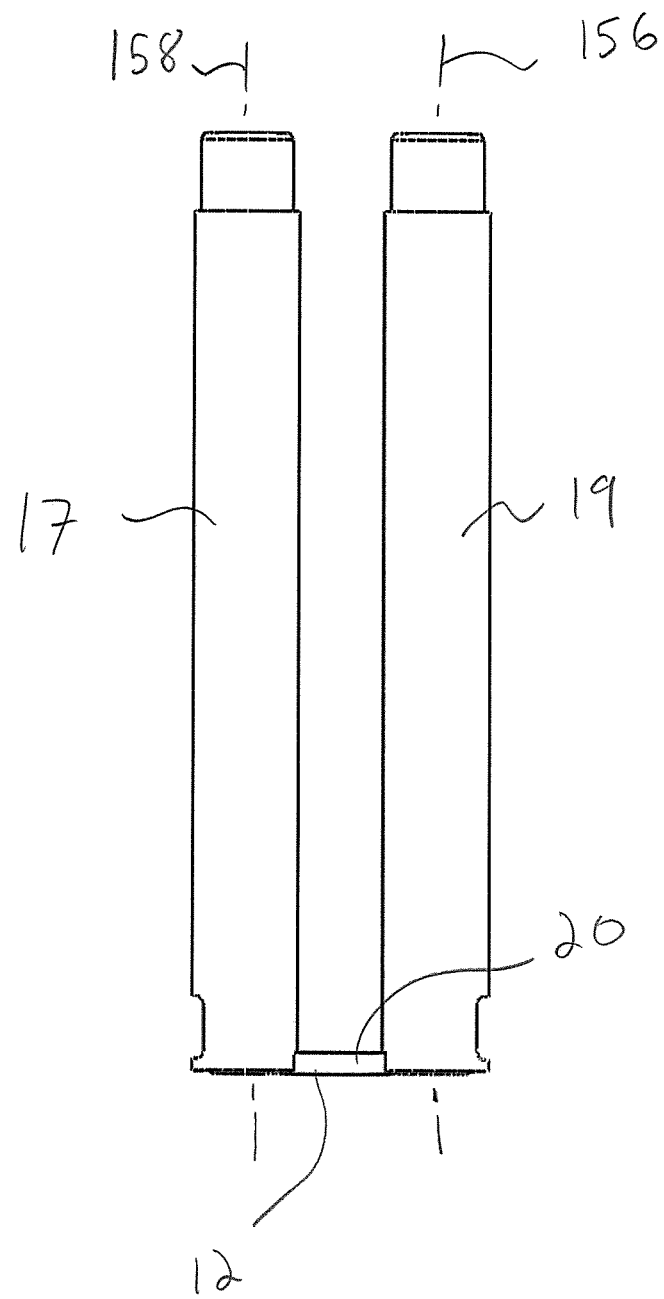
FIG. 12 is a view similar to FIG. 11 showing the manipulators pivoted toward one another to an insertion orientation which bends the intermediate portion of the bone plate and reconfigures the bone plate into a flexed configuration.
Figure 13:
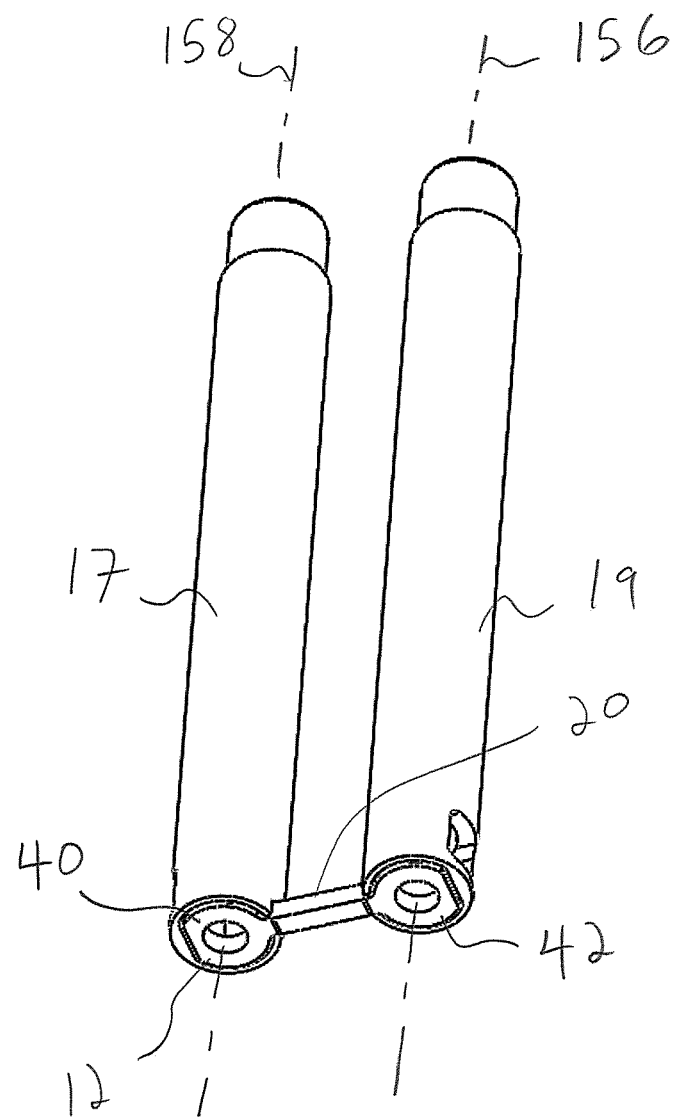
FIG. 13 is a bottom perspective view of the manipulators and bone plate of FIG. 12 showing centerlines of the manipulators aligned with through bores of the bone plate lobes.

The bone plate 12 has an initial, unflexed configuration where an intermediate portion 20 of the bone plate 12 is curved or bent, as shown in FIG. 2. With reference to FIGS. 7, 11, and 12, the bone plate 12 may be flexed using an instrument 15 that includes a pair of manipulators 17, 19. The manipulators 17, 19 are connected to the bone plate 12 and squeezed together toward an installation orientation as shown in FIG. 12, which bends the bone plate 12 to the flexed configuration wherein the intermediate portion 20 is substantially straight. This loads the intermediate portion 20 and stores potential energy in the bone plate 12 in a manner similar to compressing a spring.

Figure 17:
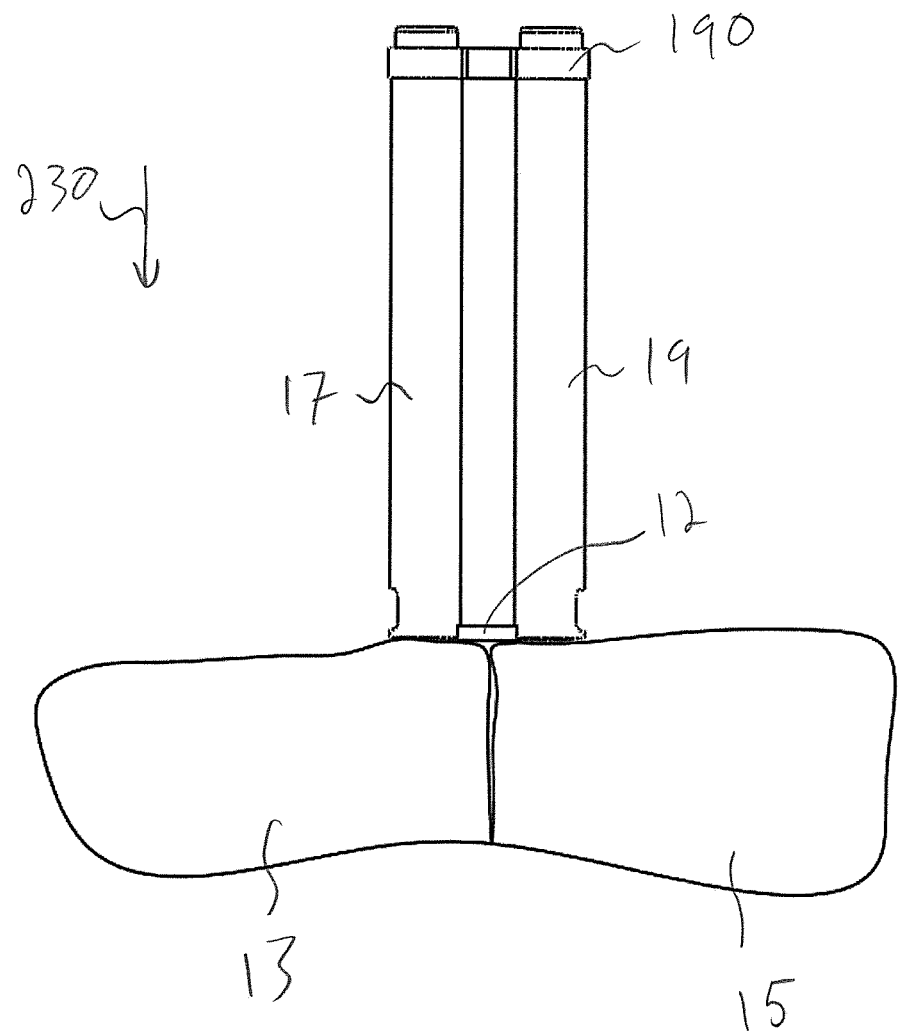
FIG. 17 is a side elevational view of the restraint and manipulators of FIG. 15 being used to position the bone plate in the flexed configuration against bones.

A restraint 190 (see FIG. 14) may be connected to the manipulators 17, 19 to hold the manipulators 17, 19 in the installation orientation which, in turn, maintains the bone plate 12 in the flexed configuration. Next, the assembled manipulators 17, 19 and restraint 190 are manipulated to position the bone plate 12 in the flexed configuration thereof against bones 13, 15, as shown in FIG. 17. The bone screws 16 are advanced through the manipulators 17, 19 and driven into throughbores 22, 24 of the bone plate 12 to secure the bone plate 12 to the bones 13, 15. With the bone plate 12 secured to the bones 13, 15 in the flexed configuration, the bone plate 12 resiliently biases against the bone screws 12 as the bone plate 12 rebounds or returns toward its unflexed configuration and the intermediate portion 20 returns in direction 30 toward its curved, unflexed shape 32, as shown by dashed lines in FIG. 23. Thus, the bone plate 12 urges the bone screws 16 together as the bone plate 12 rebounds toward its unflexed configuration which compresses the bones 13, 15 together to heal a cut or break 280. The length of the bone plate 12 may be selected so that the bone plate 12 does not completely return to its unflexed configuration after being secured to the bones 13, 15 so that the bone plate 12 continues to continuously apply compression to the bones 13, 15. Further, the intermediate portion 20 may flex as needed to accommodate subsidence or movement of the bones 13, 15 post-surgery while continuing to compress the bones 13, 15 together.

With reference to FIG. 1, the bone plate 12 has bone anchor receiving portions, such as lobes 40, 42, which include the through bores 22, 24. In one form, the bone compression device 10 includes retention mechanisms 44 to resist back-out of head portions 46 of bone screws 16 from the lobes 40, 42. In addition to resisting back-out of the bone screw head portions 46, the screw retention mechanisms 44 may also fix the bone screw head portions 46 to the bone plate lobes 40, 42. By fixing the bone screw head portions 46 to the bone plate lobes 40, 42, the bone screws 16 and bone plate lobes 40, 42 form a rigid construct with the bones 13, 15 while the intermediate portion 20 compresses the bones. This rigid construct permits a single bone plate 12 and two screws 16 to be used to stabilize bones where, in prior approaches, a pair of nitinol staples would need to be used and would involve the inefficiencies associated therewith. In one form, the screw retention mechanisms 44 includes cooperating threads on the bone screw head portion 46 and the lobes 40, 42. In another form, the screw retention mechanisms 44 may include an expandable bone screw head portion 46 and an actuator for expanding the head portion 46 into engagement with the surfaces of the through bores 22, 24, for example.

Another advantage of the bone compression device 10 is that a surgical kit of several bone compression devices 10 may be provided with fewer components than a corresponding kit of nitinol staples. The kit of bone compression devices 10 would include a plurality of bone plates 12 having different lengths, a plurality of bone screws 16 having different lengths, the manipulators 17, 19, and the restraint 190. The kit of bone compression devices 10 could have fewer components than the nitinol staple kit because the different length screws 16 in the kit could be used with any of the lengths of bone plate 12 in the kit. Thus, the kit of bone compression devices 10 would include one set of bone screws 16 of different lengths, rather than a set of bone screws 16 of different lengths for each bone plate 12. This is an improvement over a corresponding kit of nitinol staples which would include, for each staple bridge length, a set of staples with different leg lengths. The surgical kit may be provided with one length of manipulators 17, 19 that can be used with the bonne plates 12 of different lengths or may provided with a plurality of pairs of manipulators 17, 19 having different lengths. Further, the surgical kit may be provided with one or more of the restraints 190. If one restraint 190 is provided, the restraint 190 may be adjustable to fix the manipulators 17, 19 at different distances apart.

With reference to FIG. 2, the bone plate 12 is shown in an initial, unflexed configuration with the intermediate portion 20 having a non-linear, curved shape. The curved shape of the intermediate portion 20 orients center lines 50, 52 of the through bores 22, 24 to extend at an angle 53 relative to each other. The lobes 40, 42 each have an instrument receiving portion 54 including a notched profile 56 with a lip 58 and a depending flat 60. The lip 58 has a lower surface 62 that is lifted upward by a lip engaging portion 66 (see FIG. 5) of the associated manipulator 17, 19, as discussed in greater detail below.

Figure 3:
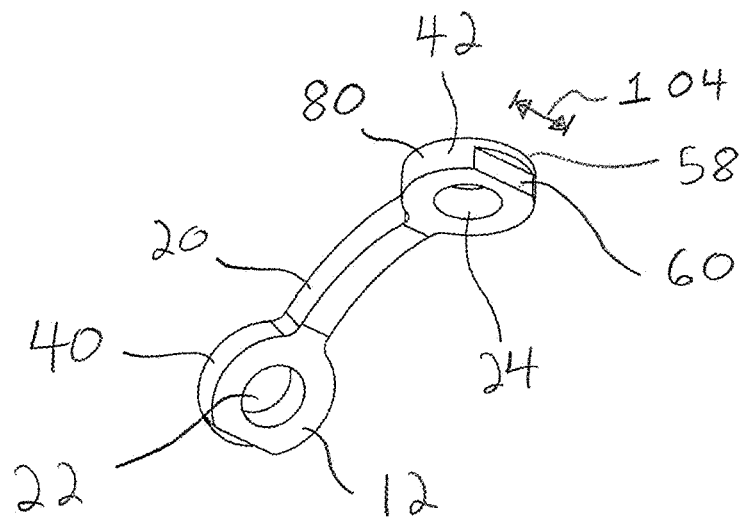
FIG. 3 is a bottom perspective view of the bone plate of FIG. 1 showing lobes of the bone plate at opposite ends of the intermediate portion and an outer lip of one of the lobes.
Figure 5:
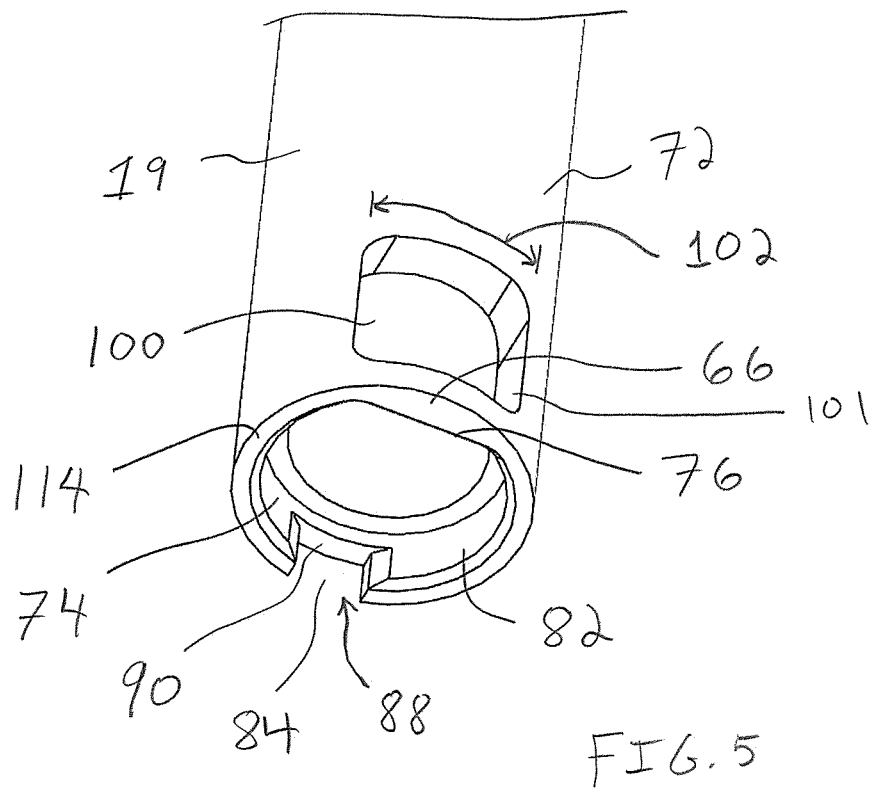
FIG. 5 is an enlarged perspective view of a distal end portion of the manipulator of FIG. 4 showing an opening sized to receive one of the lobes of the bone plate of FIG. 1.
Figure 9:
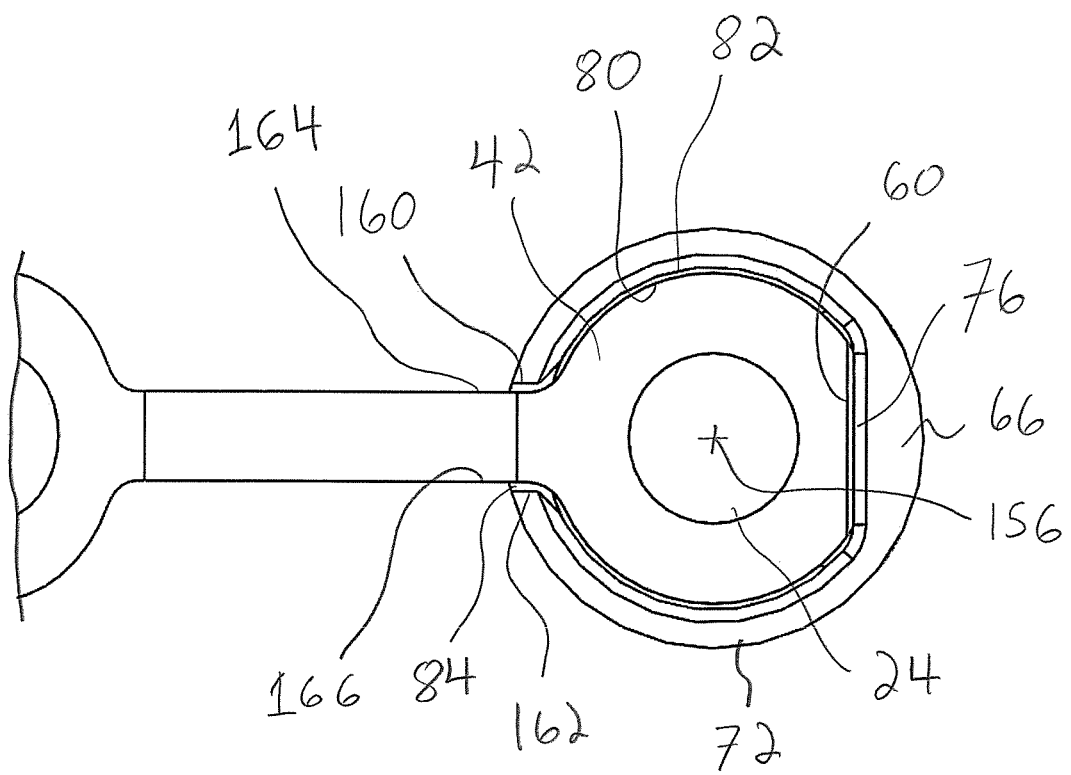
FIG. 9 is a bottom plan view of the manipulator of FIG. 8 connected to the bone plate lobe showing a mating fit of the bone plate lobe and the manipulator.

With reference to FIGS. 3 and 5, the lobes 40, 42 of the bone plate are each configured to form a mating, non-rotatable fit with a distal lobe engaging portion 72 of one of the manipulators 17, 19. Specifically, the lobe 42 has a rounded outer surface 80 that fits within a rounded inner surface 82 of the lobe engaging portion 72 of the manipulator 19. The lobes 40, 42 are sized to fit within openings 74 of the manipulators 17, 19 and the flats 60 of the lobes 40, 42 each abut a flat 76 of the associated manipulator 17, 19. The abutting flats 60, 76 of the lobes 40, 42 and manipulators 17, 19 resist turning of the lobes 40, 42 within the lobe engaging portions 72 as shown in FIG. 9.

Figure 8:
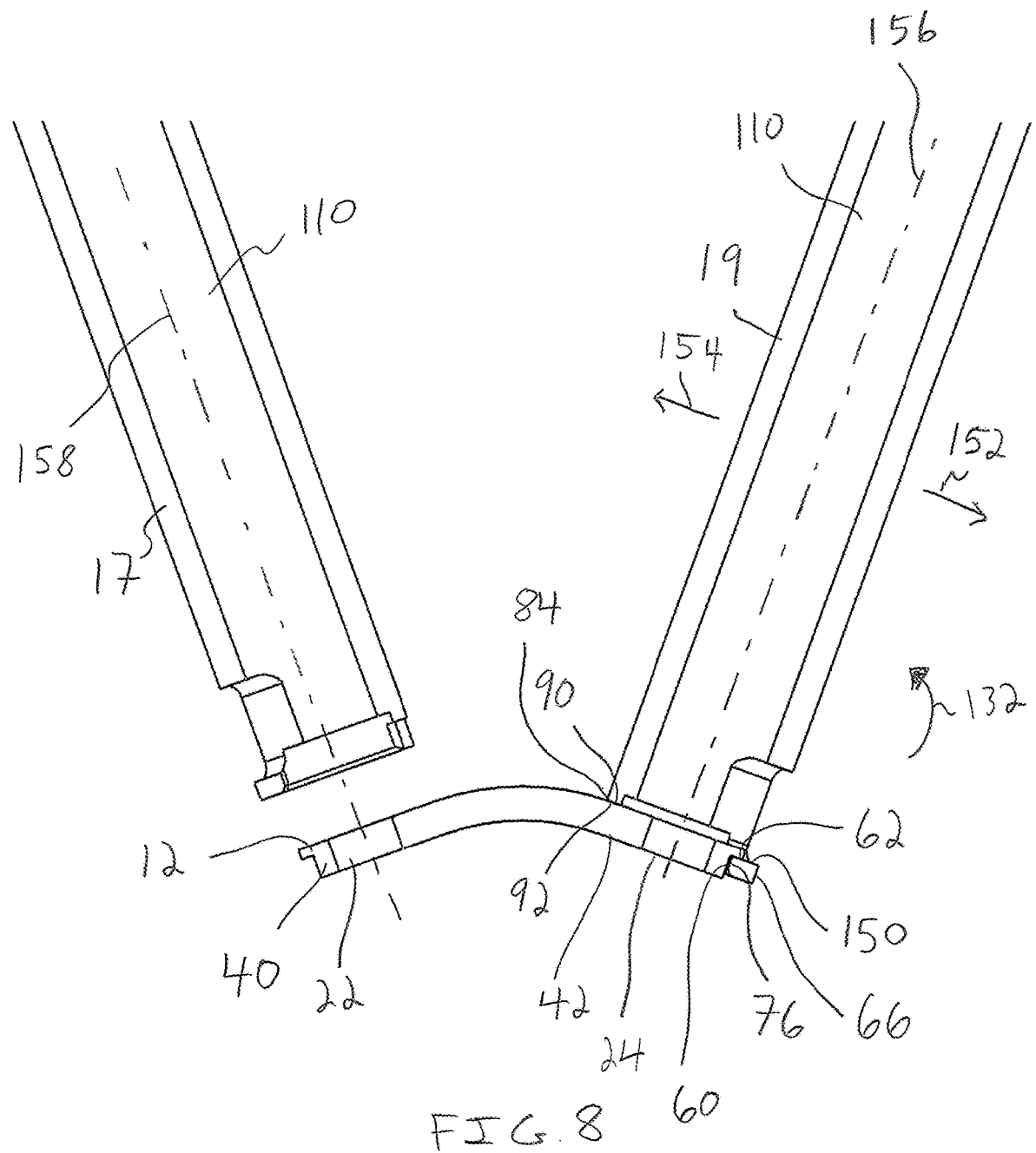
FIG. 8 is a cross-sectional view of the bone plate and manipulators of FIG. 7 showing one of the manipulators connected to the associated bone plate lobe.

With continued reference to FIGS. 3 and 5, the manipulator 19 has a notch 84 sized to receive a section of the intermediate portion 20 of the bone plate 12 as the manipulator 19 is advanced onto the lobe 42. The manipulator 19 has a fulcrum 88 for engaging the bone plate 12 as the manipulator 19 is pivoted toward the manipulator 17 to bend the bone plate 12 as discussed in greater detail below. The fulcrum 88 includes a surface 90 that rests upon an upper surface 92 of the bone plate 12, as shown in FIG. 8. Further, the notch 84 includes walls 160, 162 arranged to abut sides 164, 166 of the intermediate portion 20 and resist rotational movement between the lobe 24 and the manipulator 19.

Figure 18:
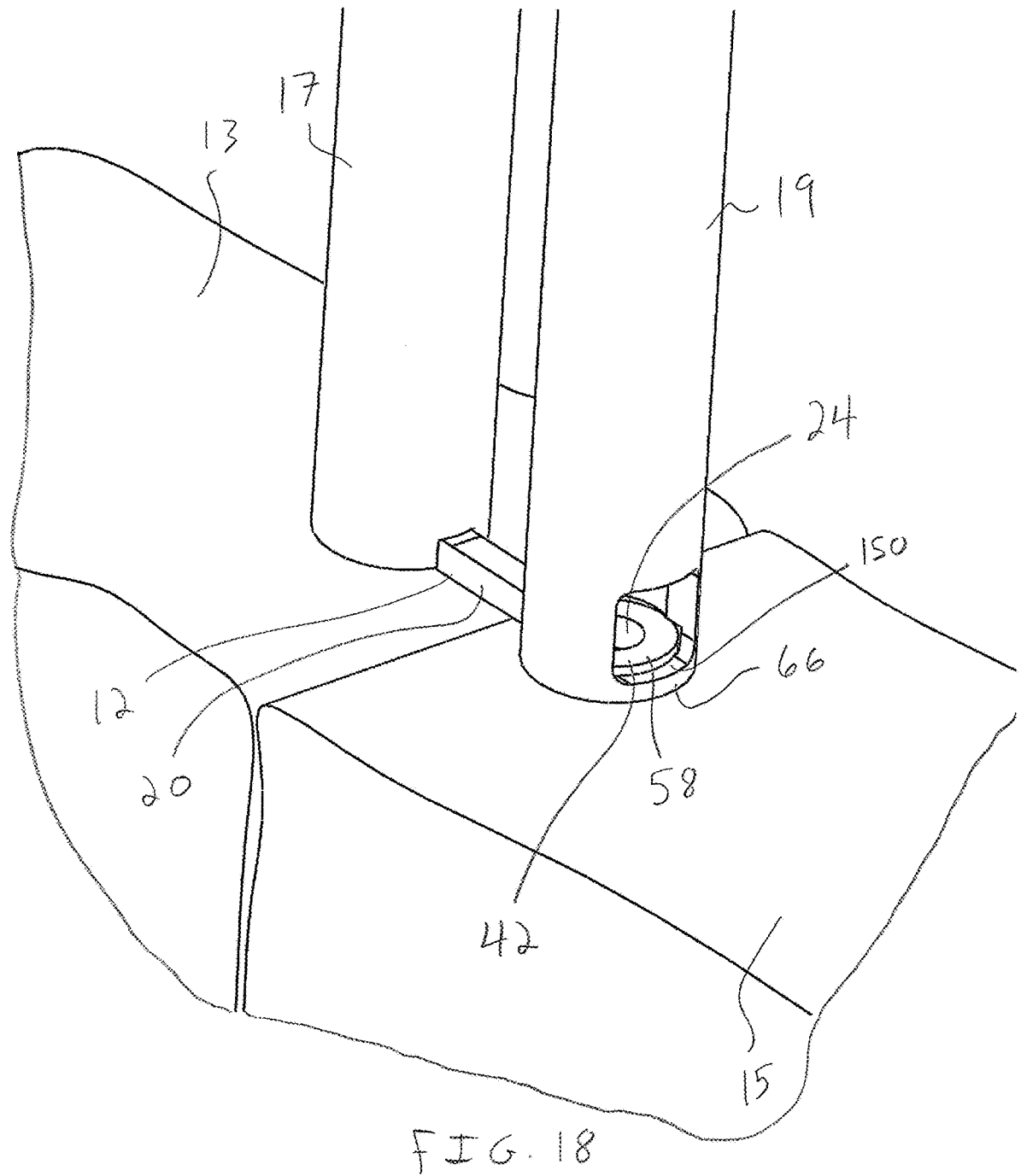
FIG. 18 is an enlarged perspective view showing the manipulators of FIG. 17 maintaining the bone plate in the flexed configuration against the bones.

Returning to FIG. 5, the manipulator 19 has an aperture 100 sized to receive the lip 58 of the lobe 42. The aperture 100 has a width 102 larger than a width 104 (see FIG. 3) of the lip 58. Turning to FIGS. 8 and 18, the lip 58 of the lobe 42 extends over and is supported on an upper surface 150 of the lip engaging portion 66 with the lip 58 positioned in the aperture 100 such that pivoting of the manipulator 19 in direction 132 tightly engages the lip lower surface 62 and the upper surface 150 (see FIG. 8).

Figure 4:
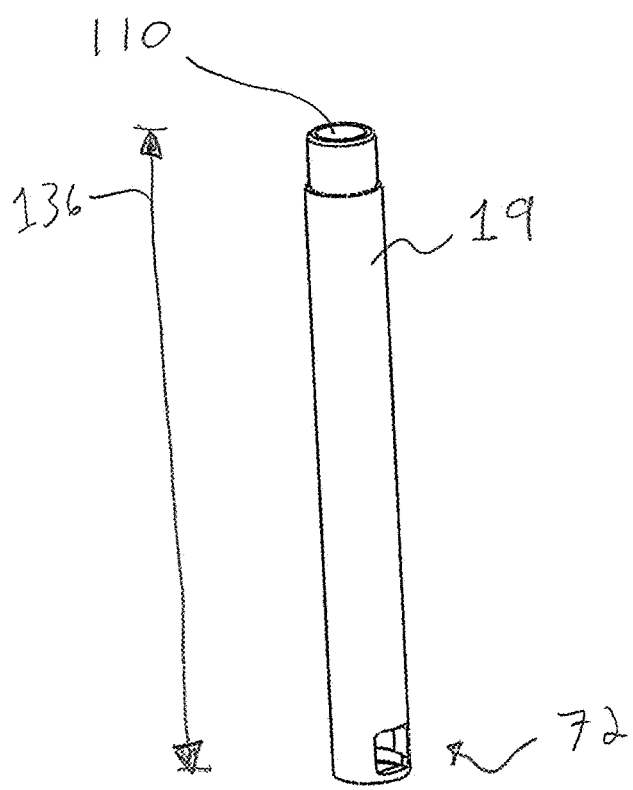
FIG. 4 is a perspective view of one of a pair of manipulators for implanting the bone plate of FIG. 1.
Figure 6:
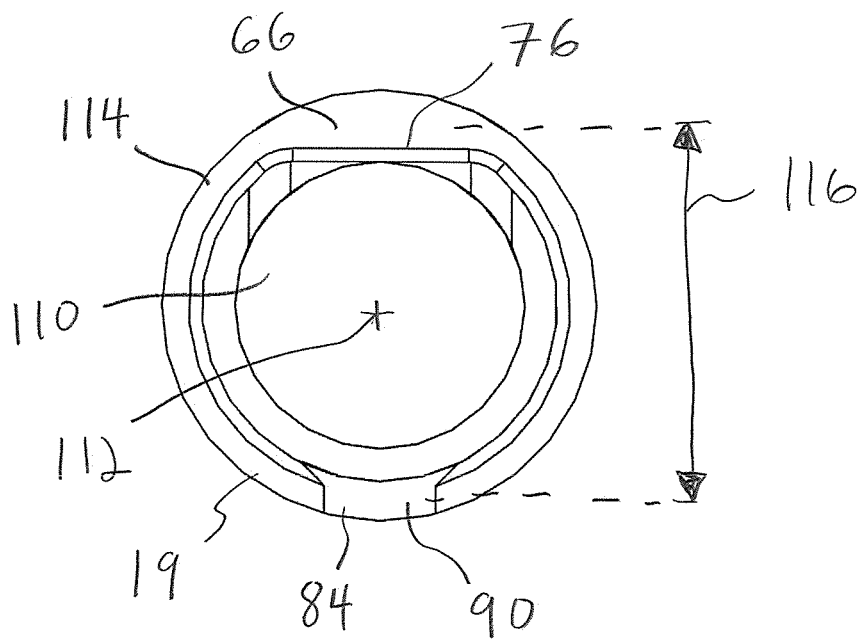
FIG. 6 is a bottom plan view of the distal end portion of the manipulator of FIG. 4 showing a central cannula of the manipulator.

With reference to FIG. 6, the manipulator 19 has a cannula 110 with a center 112 and a wall 114 extending about the cannula 110. As noted above, the lip engaging portion 66 of the manipulator 19 engages the lip lower surface 62 of the lobe 42 and the surface 90 of the manipulator 19 seats on the upper surface 92 of the bone plate 12 with the manipulator 19 connected to the lobe 42. To provide leverage to bend the bone plate 12, the manipulators 17, 19 have a distance 116 between the lip engaging portion 66 and the surface 90 of each manipulators 17, 19. In this manner, pivoting the manipulators 17, 19 in directions 130, 132 as shown in FIGS. 11 and 12 tends to pull upwardly on the lip 58 and pushes downwardly on the upper surface 92 of the bone plate 12 which straightens out the bone plate intermediate portion 20. Additionally, the manipulators 17, 19 have a length 136 that provides additional leverage for bending the bone plate 12 as shown in FIG. 4.

With reference to FIGS. 7-23, a method of applying compression to the bones 13, 15 using the bone plate 12 is shown. Initially, the lobe engaging portions 72 of the manipulators 17, 19 are connected to the lobes 40, 42 of the bone plate 12. With reference to FIG. 7, the manipulator 19 is maneuvered in direction 140 to position the lip engaging portion 66 in the notched profile 56 of the lobe 42 below the lip 58. With the lip engaging portion 66 engaged with the underside of the lip 58, the manipulator 19 is then pivoted in direction 142 which shifts the notch 84 downward onto the intermediate portion 20 of the bone plate 12 and seats the lobe engaging portion 72 on the lobe 42.

With reference to FIG. 8, the manipulator 19 is shown after pivoting in direction 142 such that the upper surface 150 of the lip engaging portion 66 is engaged with the lower surface 62 of the lip 58, the flat 76 of the manipulator 19 is engaged with the flat 60 of the lobe 42, and the surface 90 of the manipulator 19 is engaged with the upper surface 92 of the bone plate 12. The lip engaging portion 66 engages the bone plate 12 at one side of the lobe 42 and the notch 84 engages the intermediate portion 20 at the opposite side of the lobe 42. This engagement resists lateral movement between the lobe 42 and the manipulator 19 in directions 152, 154 even as the manipulator 19 is pivoted to bend the bone plate 12. Further, this engagement maintains a coaxial alignment of a center line of the lobe through bore 24 and a center line of the manipulator cannula 110. The aligned center lines of the through bore 24 and cannula 110 will be referred to with combined reference numeral 156. The manipulator 17 is then connected to the lobe 40 in a similar manner and establishes a coaxially aligned center line 158 of the through bore 22 of the lobe 40 and the cannula 110 of the manipulator 17.

Figure 10:
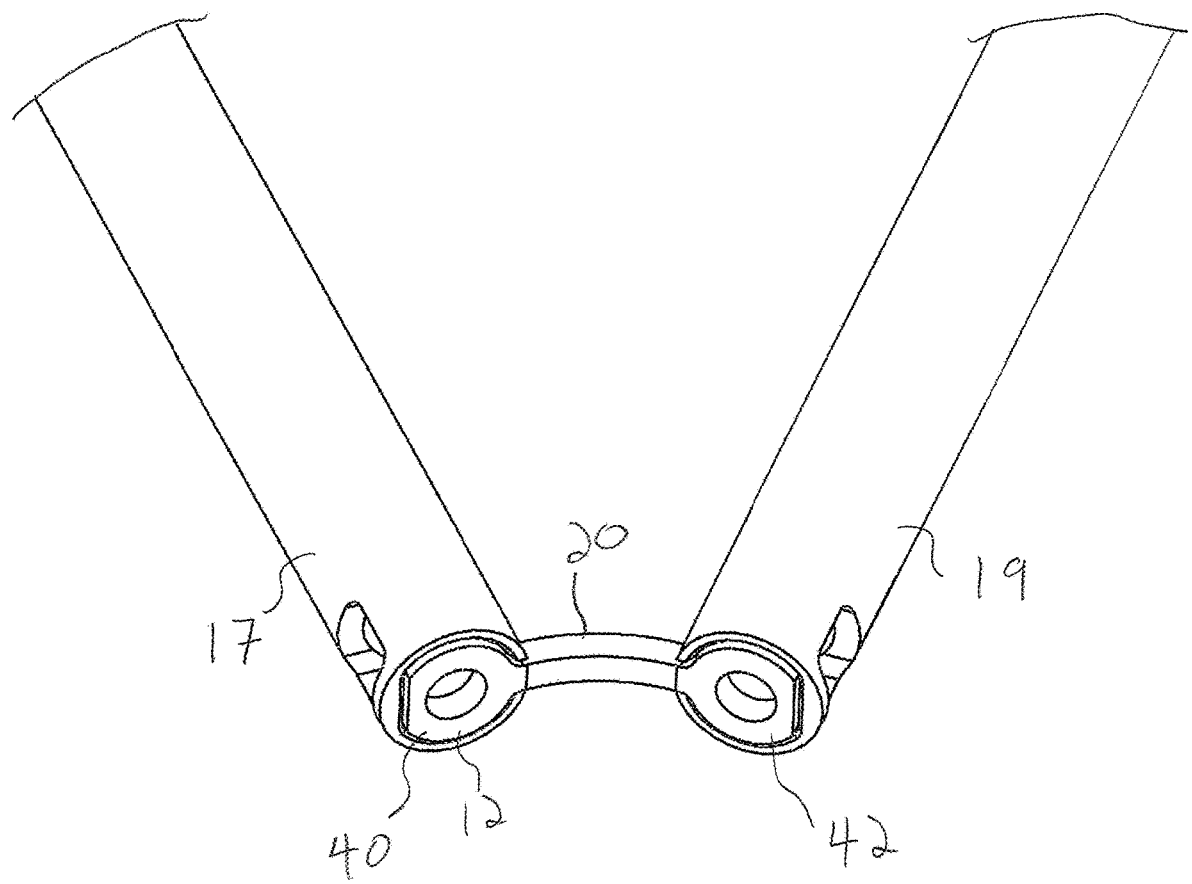
FIG. 10 is a bottom perspective view showing both of the manipulators of FIG. 7 connected to the lobes of the bone plate.

With reference to FIGS. 10 and 11, the manipulators 17, 19 are shown connected to the lobes 40, 42 of the bone plate 12. At this point, the bone plate 12 is in the initial, unflexed configuration and the intermediate portion 20 of the bone plate 12 has a curved shape. With the bone plate 12 in the unflexed configuration, the center lines 156, 158 are oriented at an angle 170 that may be the same or substantially the same as the angle 53 between the centerlines 50, 52 of the bone plate throughbores 22, 24 with the bone plate 12 in the unflexed configuration (see FIG. 2).

Next, the manipulators 17, 19 are pivoted toward each other in directions 130, 132 such as by a user squeezing the manipulators 17, 19 together, into an installation orientation as shown in FIG. 12. With the manipulators 17, 19 in the installation orientation, the centerlines 156, 158 may be substantially parallel to each other, as shown in FIG. 12. Comparing FIGS. 11 and 12, pivoting the manipulators 17, 19 toward each other flexes the bone plate 12 and bends the intermediate portion 20 into a straight configuration. With the bone plate 12 in the flexed configuration of FIG. 12, the bone plate 12 is generally planar which is in contrast to the bent configuration of the bone plate 12 shown in FIG. 2.

It will be appreciated that the bone plate 12 may have a flexed configuration for some procedures where the bone plate 12 is partially flexed and the intermediate portion 20 is only partially straightened. Even when the intermediate portion 20 is only partially straightened, the elastic properties of the bone plate 12 will still apply a constant, compressive force against the bones 13, 15 once the bone plate 12 has been secured to the bones 13, 15.

Figure 14:
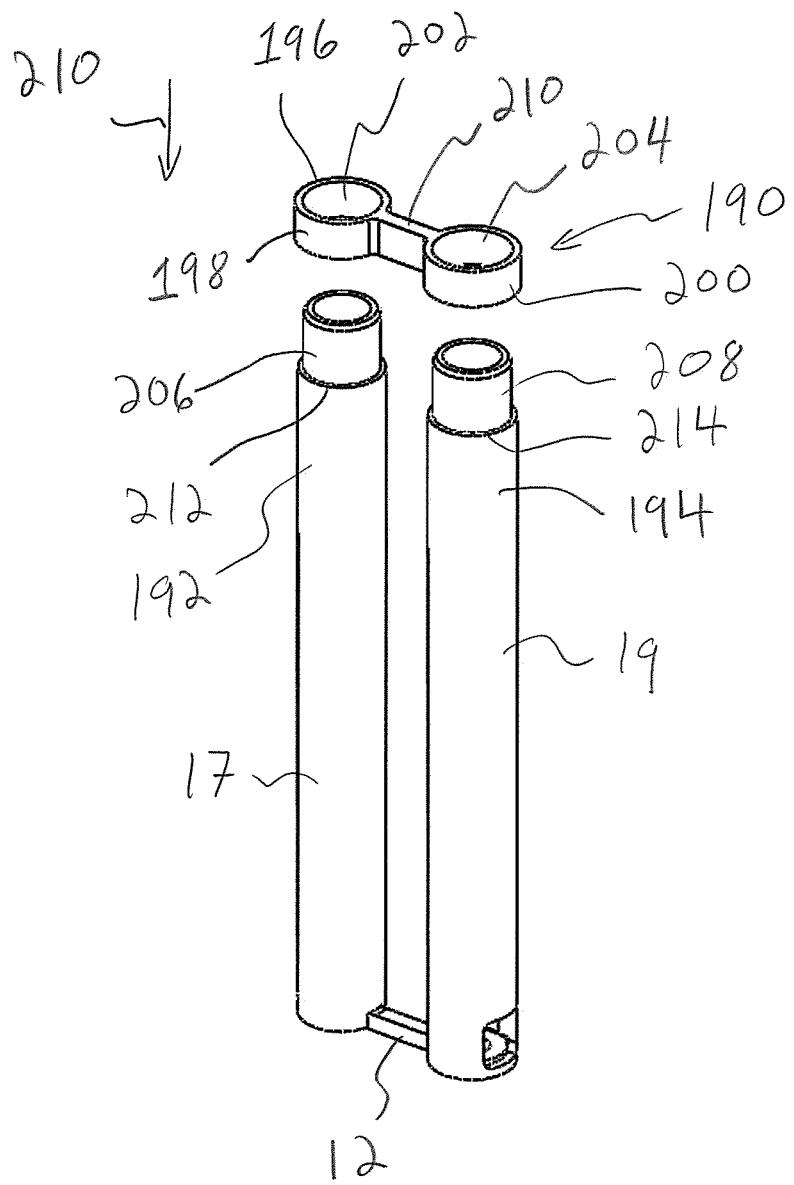
FIG. 14 is a perspective view of the manipulators and bone plate of FIG. 12 showing a restraint being advanced onto the manipulators to secure the manipulators in the insertion orientation.
Figure 15:
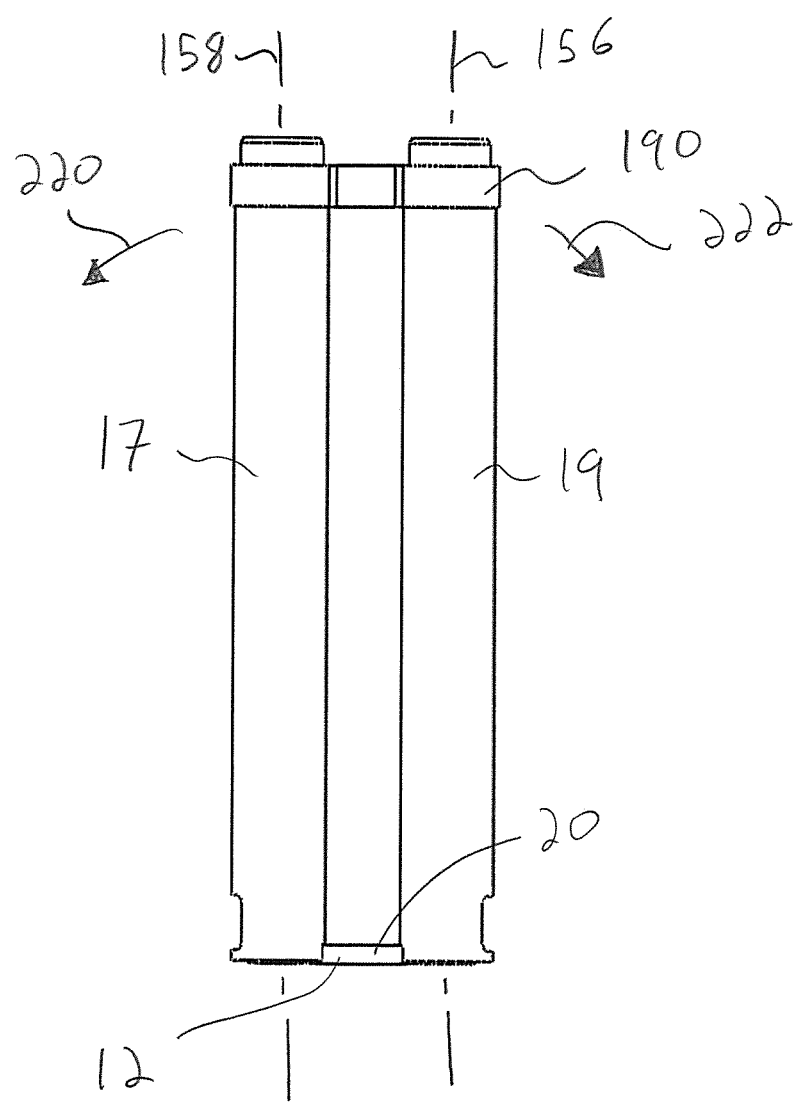
FIG. 15 is a side view similar to FIG. 14 showing the restraint resisting pivoting of the manipulators away from the insertion orientation thereof.

To maintain the manipulators 17, 19 in the installation orientation and keep the bone plate 12 in the flexed configuration, a restraint 190 may be connected to proximal end portions 192, 194 of the manipulators 17, 19. As shown in FIGS. 14 and 15, the restraint 190 has collars 198, 200 and a link portion 210 connecting the collars 198, 200. The restraint 190 is connected to the manipulators 17, 19 by advancing the restraint 190 in direction 210 so that the collars 198, 200 fit over necks 206, 208 of the manipulators 17, 19 and rest against shoulders 212, 214 of the manipulators 17, 19. The restraint 190 resists pivoting of the manipulators 17, 19 in directions 220, 222 away from the installation orientation, as shown in FIG. 15. The manipulators 17, 19 and restraint 190 may be made materials, such as metals or polymers, sufficiently rigid to resist the resilient bending of the bone plate 12 back toward its initial, unflexed configuration. For example, the manipulators 17, 19 may be made of stainless steel and the restraint 190 may be made from carbon fiber polyether ether ketone (PEEK). Further, the manipulators 17, 19 and restraint 190 may be disposable or reusable.

Figure 16:
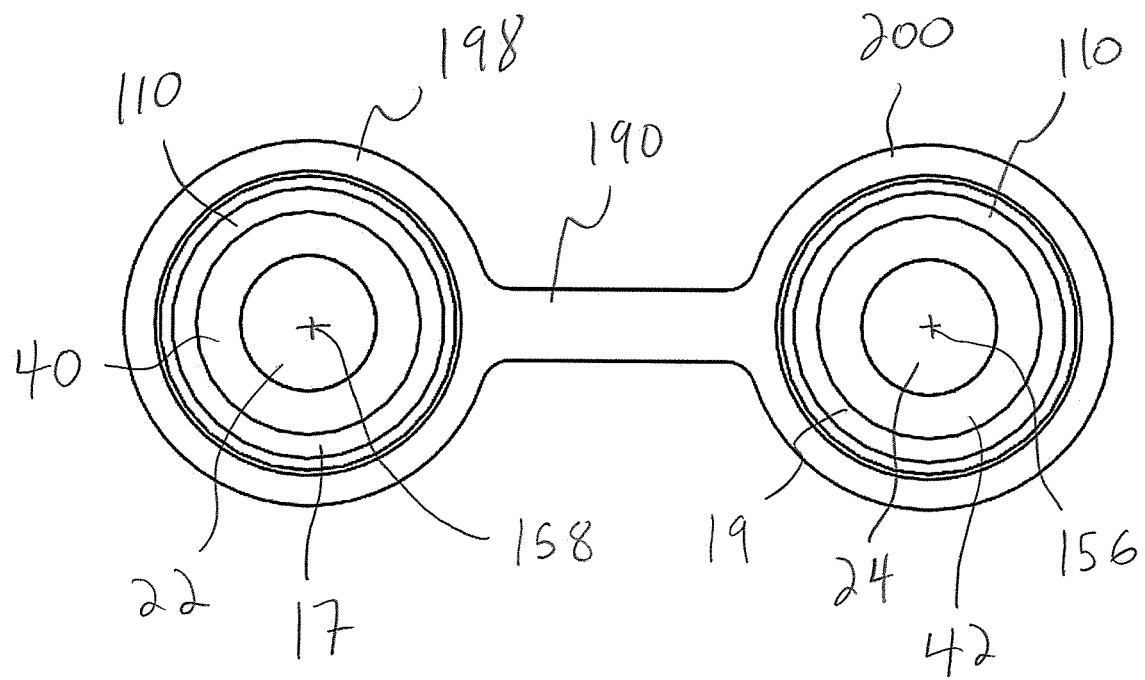
FIG. 16 is a top plan view of the restraint, manipulators, and bone plate of FIG. 15 showing cannulas of the manipulators aligned with the through bores of the bone plate lobes.

With reference to FIG. 16, the collars 198, 200 may fit around the exteriors of the necks 206, 208 of the manipulators 17, 19 which permits the cannulas 110 of the manipulators 17, 19 to be unobstructed with the restraint 190 connected to the manipulators 17, 19. The unobstructed cannulas 110 permit access to the through bores 22, 24 of the lobes 40, 42 through the cannulas 110.

With reference to FIGS. 17 and 18, the restraint 190 maintains the manipulators 17, 19 and bone plate 12 in an assembled configuration and permits one-handed handling of the assembly of the bone plate 12, manipulators 17, 19, and restraint 190. This assembly of the restraint 190, manipulators 17, 19 and bone plate 12 can be readily maneuvered in direction 230 into position on the bones 13, 15. As shown in FIG. 18, the intermediate portion 20 of the bone plate 12 is in its generally straight or flat configuration due to the restraint 190 continuing to resist pivoting of the manipulators 17, 19 away from their installation orientation.

As shown in FIG. 18, the manipulators 17, 19 have been used to position the bone plate 12 on the bones 13, 15 such that the through bores 22, 24 are each positioned over one of the bones 13, 15. Due to the elastic properties of the bone plate 12, the intermediate portion 20 biases the lobes 40, 42 back toward their unflexed orientations (see FIG. 2). The engagement of the notches 84 and lip engaging portions 66 of the manipulators 17, 19 resist the lobes 40, 42 returning to the unflexed orientations which causes the intermediate portion 20 to press upwardly against the surface 90 of the manipulators 17, 19 and the lips 58 of the lobes 40, 42 to press downwardly against the lip engaging portion 66 of the manipulators 17, 19.

Figure 19:
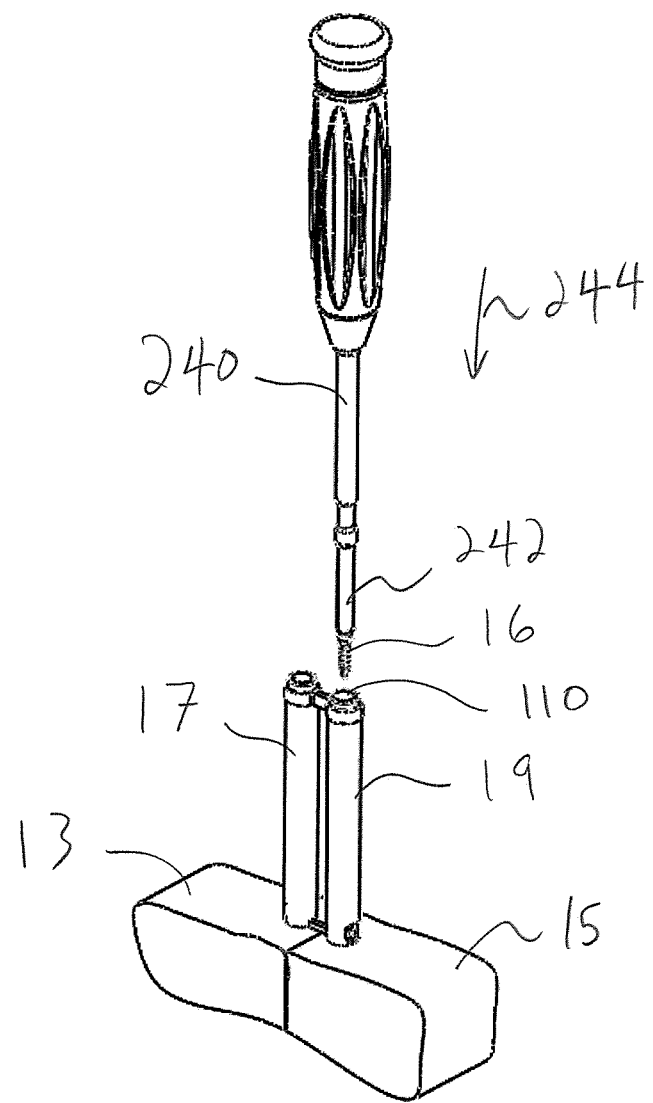
FIG. 19 is a schematic view of a screw driver positioned to advance a bone screw through a cannula of one of the manipulators.
Figure 20:
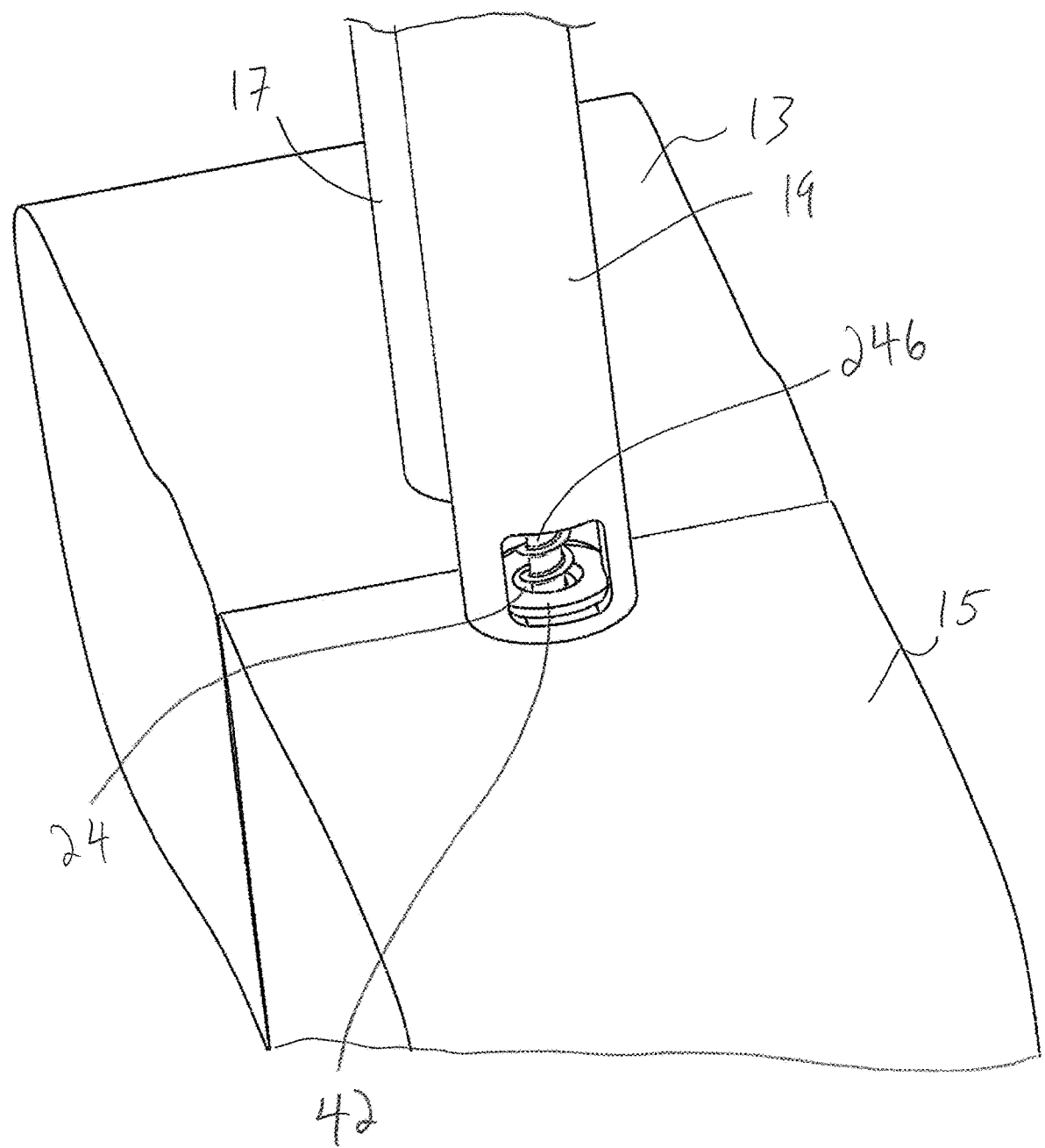
FIG. 20 is a perspective view similar to FIG. 18 showing a shank portion of the bone screw being driven into the through bore of one of the bone plate lobes.
Figure 21:
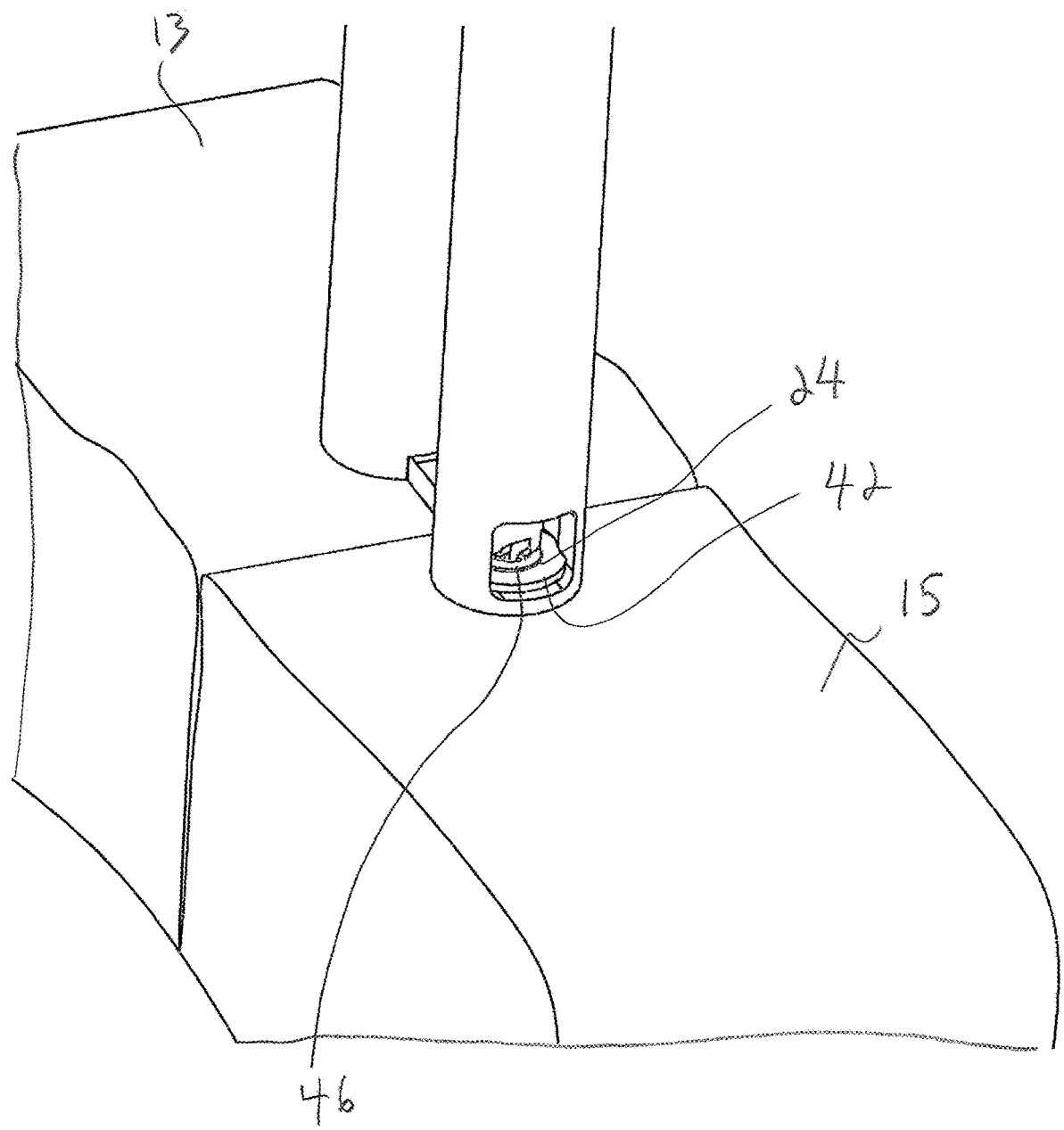
FIG. 21 is a view similar to FIG. 20 showing the screw driver driving a head portion of the bone screw into the lobe through bore.

With reference to FIGS. 19 and 20, an instrument, such as a screw driver 240, has a shaft 242 with a bone screw 16 connected thereto. The screw driver 240 and bone screw 16 are advanced in direction 244 into the cannula 110 of manipulator 19 to advance a shank portion 246 of the bone screw 16 into the through bore 24 of the lobe 42 and drive the shank portion 246 into the bone 15. The screw driver 240 continues to drive the bone screw 16 into the bone 15 until the head portion 46 of the bone screw 16 seats within the through bore 24 of the lobe 42, as shown in FIG. 21. This process is repeated to drive the other bone screw 16 into the through bore 22 of the lobe 40 so that both lobes 40, 42 are secured to the bones 13, 15 as shown in FIG. 22.

Figure 22:
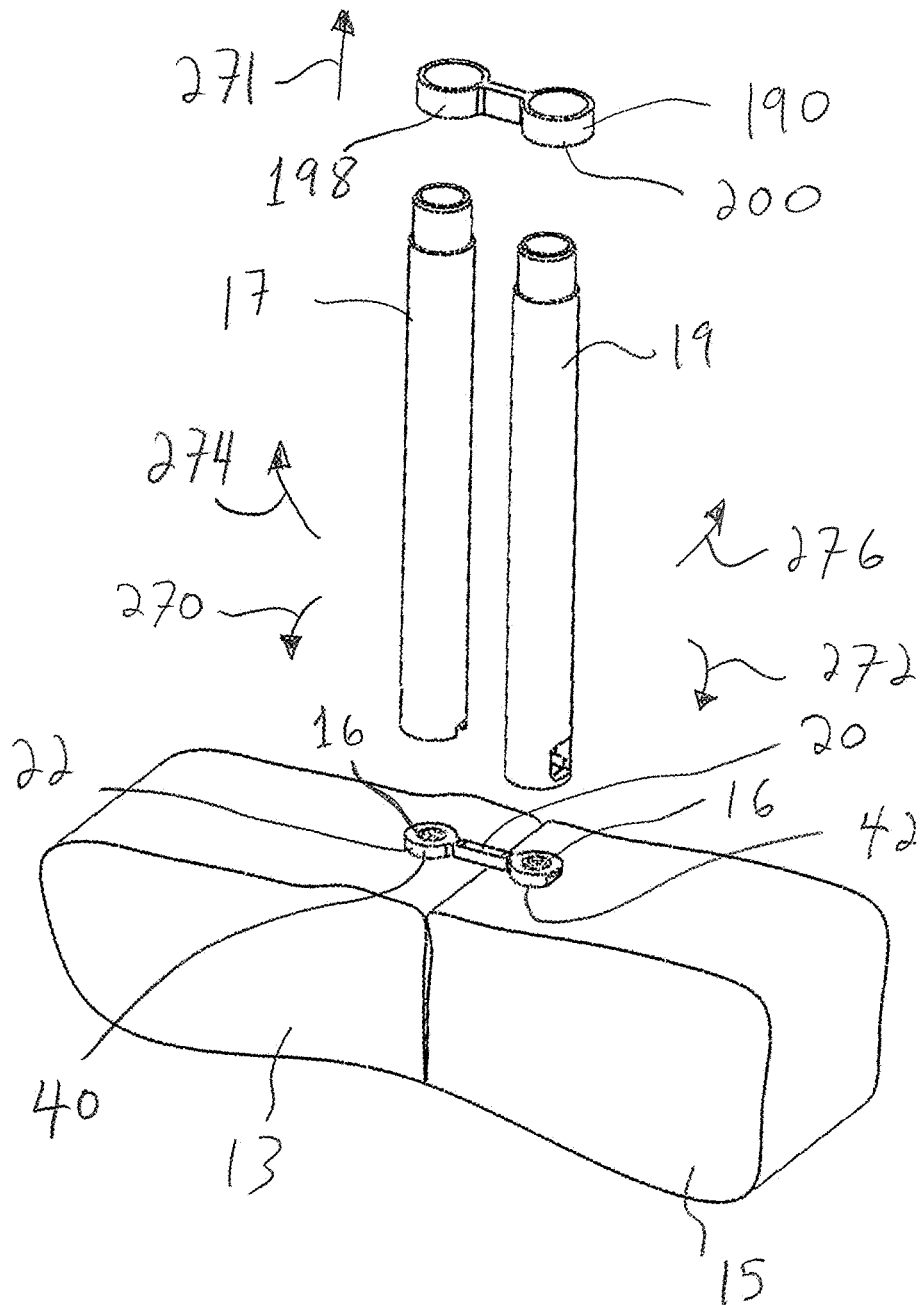
FIG. 22 is a schematic view showing the bone plate in the flexed configuration having been secured to the bone by the bone screws and the manipulators having been disconnected from the bone plate lobes.

Once the bone plate 12 in the flexed configuration has been secured to the bones 13, 15 the restraint 190 is removed in direction 271 to draw the collars 198, 200 off of the necks 206, 208 as shown in FIG. 22. The bone plate engaging members 17, 19 are pivoted in directions 270, 272 to lift the notches 84 of the manipulators 17, 19 off of the intermediate portion 20 of the bone plate 12. Next, the manipulators are shifted outwardly in directions 274, 276 in order to unhook the lip engaging portions 66 from below the lips 58 of the lobes 40, 42.

Figure 23:
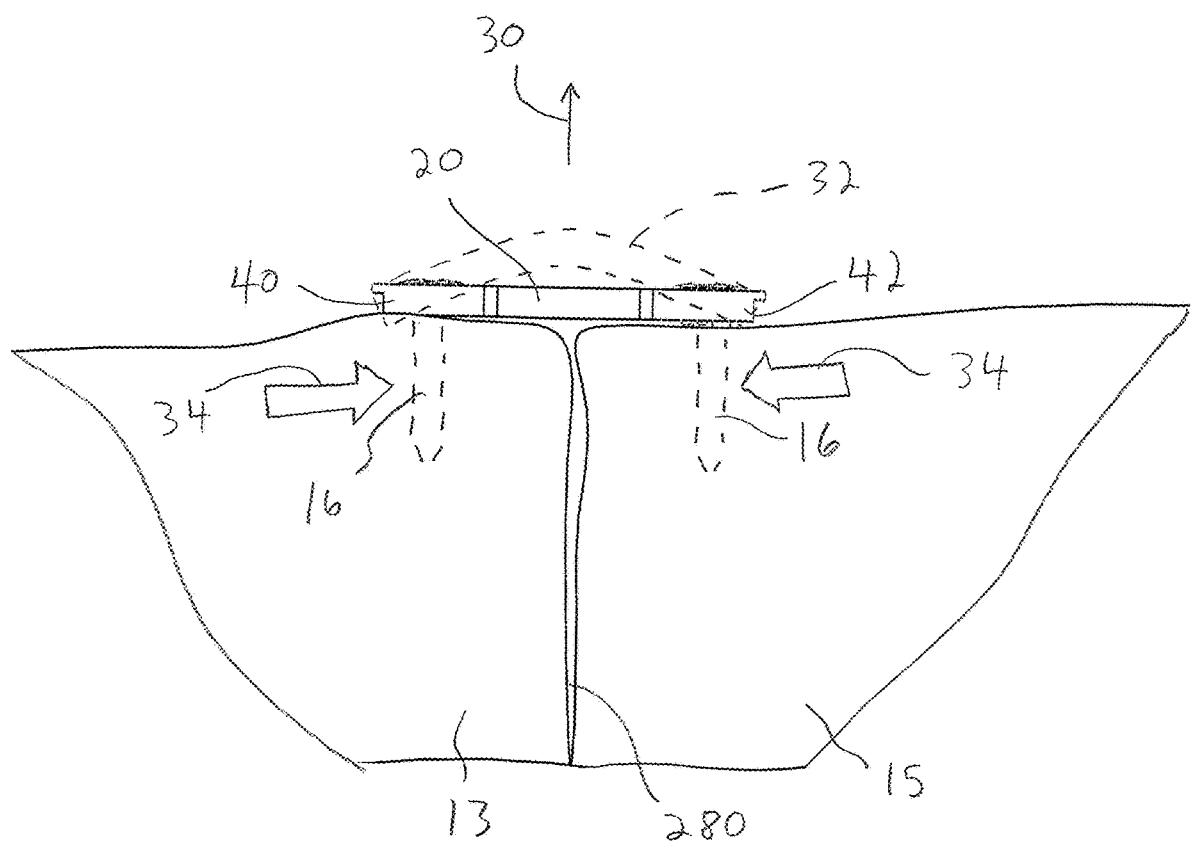
FIG. 23 is a side elevational view of the bone plate of FIG. 22 secured to the bones in the flexed configuration with dashed lines showing the bone plate shifting toward the unflexed configuration thereof and compressing the bones together.

With reference to FIG. 23, the bone plate 12 in the flexed configuration is shown secured to the bones 13, 15. The bone screws 16 have been driven into the bones 13, 15 to secure the lobes 40, 42 against the bones 13, 15. Due to the elastic properties of the bone plate 12, the intermediate portion 20 returns toward its unflexed configuration 32. As the intermediate portion 20 bends upwardly from the bones 13, 15, the bone plate 12 applies tension to the bone screws 16 and compresses the bones 13, 15 together.

In another approach, the bone plate 12 may be made of a shape memory nitinol that shifts in situ from a flexed, installation configuration to an unflexed, compression configuration in response to the temperature of the patient. The bone plate 12 may be chilled, such as in a saline solution, mechanically forced into a straightened configuration, and implanted in the straightened configuration. As the temperature of the bone plate 12 raises to the internal temperature of the patient, the bone plate 12 will return to its original shape and compress the bones 13, 15.

Figure 24:
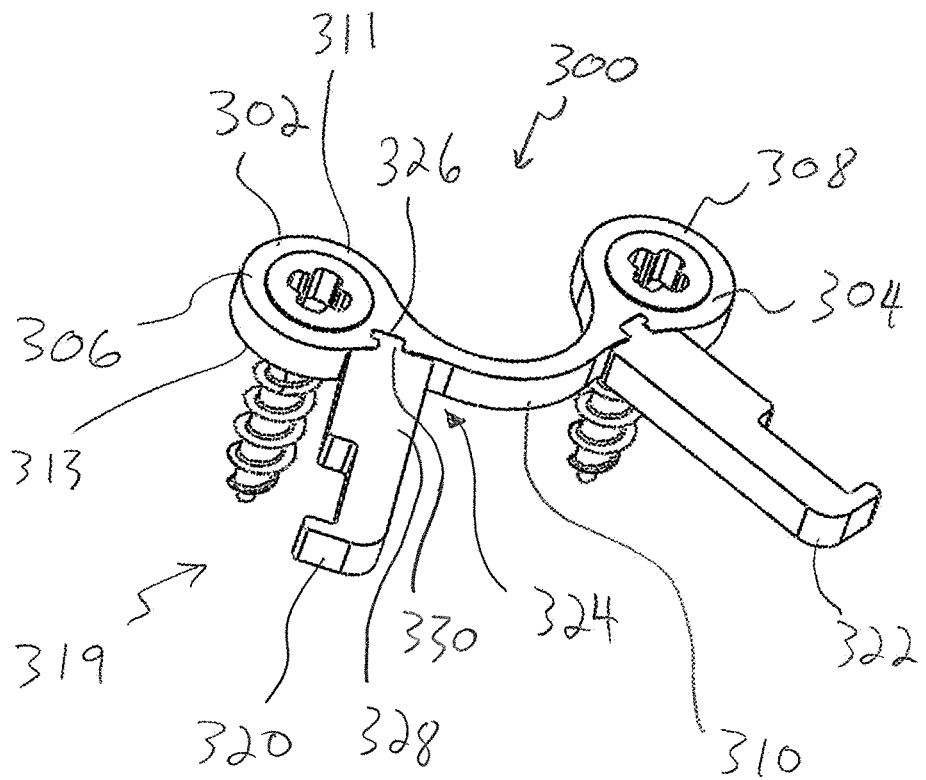
FIG. 24 is a perspective view of a bone compression device including a bone plate and manipulators that are releasably connectable to the bone plate.

With reference to FIG. 24, a bone compression device 300 is provided having a bone plate 302 that flexes within the thickness of the bone plate 302 to apply compression to bones. The bone plate 302 has a body 304 with lobes 306, 308 and an intermediate portion 310 connecting the lobes 306, 308. In the unflexed configuration of the bone plate 302, the intermediate portion 310 is curved or bent and extends between planes defined by upper and lower surfaces 311, 313 of the lobes 306, 308.

To flex the bone plate 302 to a flexed configuration, an instrument 319 is provided including manipulators 320, 322 that each have a releasable connection 324 to the bone plate 302. The releasable connection 324 includes a recess 326 of the bone plate 302 and a complimentary projection 330 of the associated manipulator 320, 322 configured to form an interlocking, rigid engagement with the recesses 326.

Figure 25:
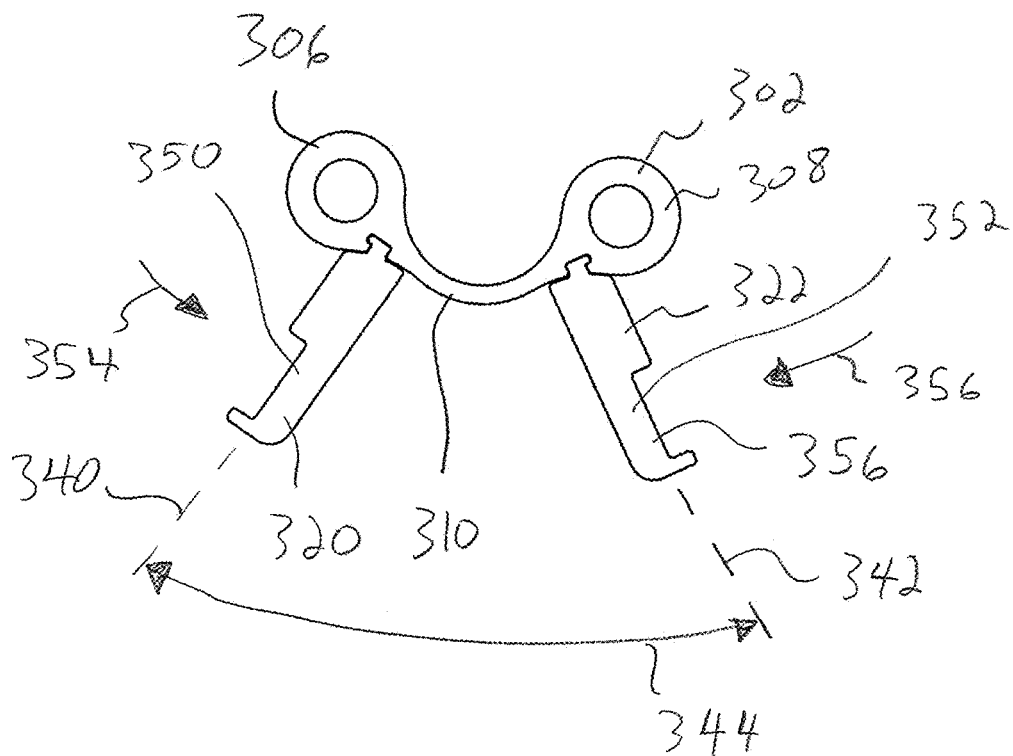
FIG. 25 is a top plan view of the bone plate of FIG. 24 showing the bone plate in an unflexed configuration with an intermediate portion of the bone plate curved.

With reference to FIG. 25, the bone plate is shown in the initial, unflexed configuration. With the manipulators 320, 322 connected to the bone plate 302, longitudinal axis 340, 342 of the manipulators 320, 322 extend an angle 344 to one another.

Figure 26:
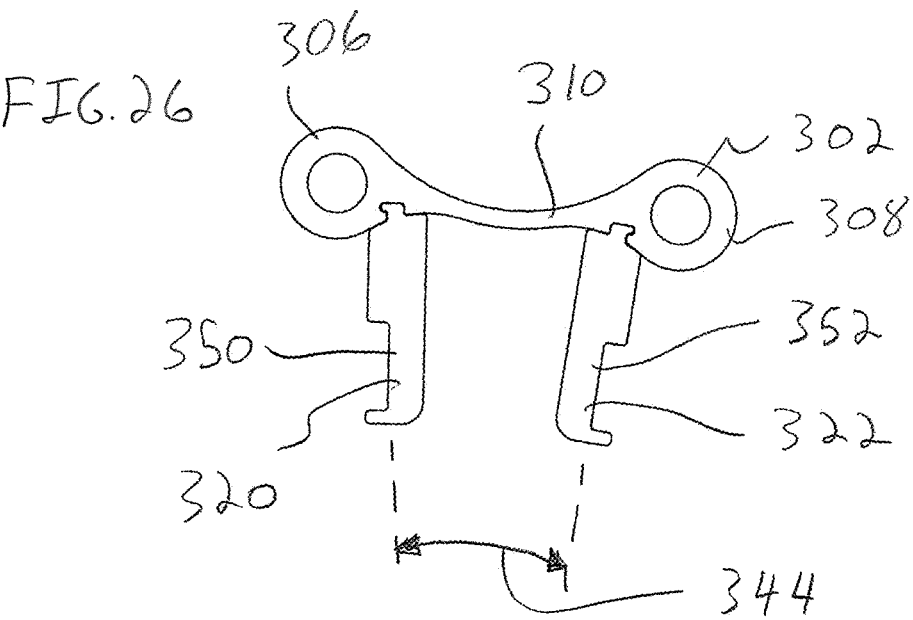
FIG. 26 is a top plan view similar to FIG. 25 showing the manipulators squeezed together which flexes the bone plate and straightens the intermediate portion of the bone plate.

Next, handle portions 350, 352 of the manipulators 320, 322 are grasped and pressed toward one another in directions 354, 356 from an initial orientation to an installation orientation. Because the manipulators 320, 322 are connected to the lobes 306, 308, pressing the manipulator handle portions 350, 352 together deflects the intermediate portion 310 from the initial, curved configuration as shown in FIG. 24 to a flexed, straightened configuration as shown in FIG. 26. As the bone plate 302 flexes between the unflexed and flexed configurations, the intermediate portion 310 remains between the planes defined by the upper and lower surfaces 311, 313 of the lobes 306, 308. With the bone plate 302 in the flexed configuration, a user may hold the manipulators 320, 322 in the installation orientation and keep the bone plate 302 in the flexed configuration with one hand, e.g., between a thumb and an index finger.

Figure 27:
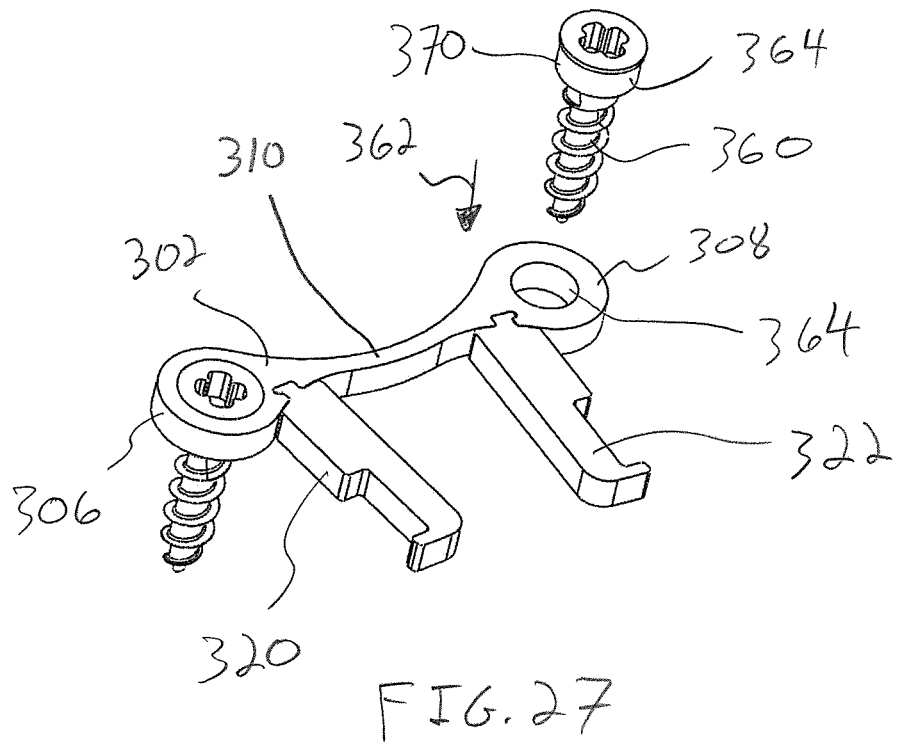
FIGS. 27 and 28 are perspective views of the bone plate and manipulators of FIG. 26 showing a bone screw being driven into a through bore of the bone plate while the manipulators hold the bone plate in the flexed configuration.
Figure 28:
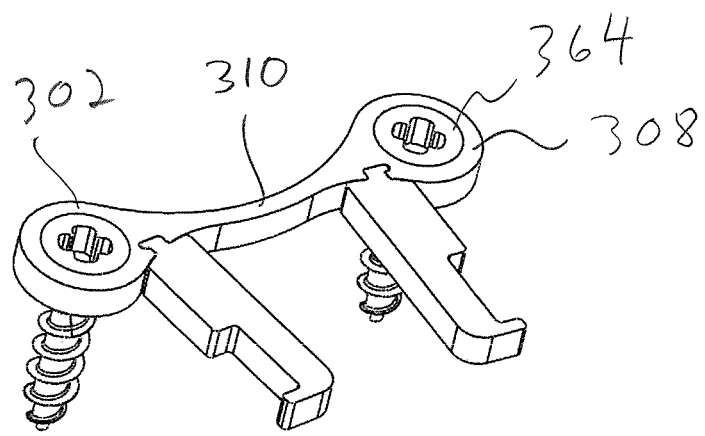

With reference to FIGS. 27 and 28, the flexed bone plate 302 has been positioned on bones (not shown) and bone screws 360 are advanced in direction 362 into through bores 364 of the lobes 306, 308. Once the bone plate 302 has been secured to bones, the lobes 306, 308 may turn slightly about a bone screw head portion 364 as the intermediate portion 310 bends back toward its curved, unflexed configuration and compresses the bones together via the bone screws 360. To accommodate this slight turning of the lobes 306, 308 about the head portions 364, the head portions 360 may have a non-threaded outer surface 370. If desired, screw retention mechanisms may be provided to resist backout of the bone screws 360 from the through bores 364 while permitting this turning of the lobes 306, 308 about the head portion 364. For example, the lobes 306, 308 may each have a lip extending about the through bore 364 that deflects out of the way of the bone screw 306 as the bone screw 306 is advanced into the through bore 364 and then snaps back over the head portion 364 once the head portion 364 is seated within the through bore 364.

Figure 29:
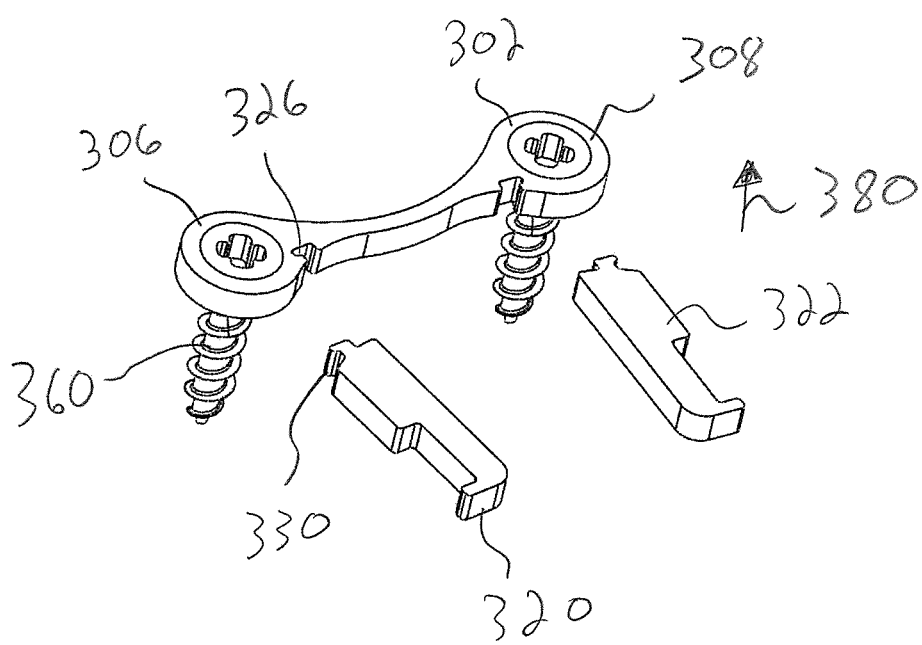
FIG. 29 is a perspective view similar to FIGS. 27 and 28 showing the manipulators disconnected from the bone plate after the bone plate has been implanted in the flexed configuration thereof.

With reference to FIG. 29, once the bone plate 302 has been secured to the bones via the bone screws 360, the manipulators 320, 322 may be disconnected from the bone plate 302. For example, the projections 330 may be slid in direction 380 out of the recesses 326. At this point, the flexed intermediate portion 310 biases against the bone screws 360 and compresses the bone screws 360 and bones connected thereto together as the intermediate portion returns toward its initial, unflexed configuration. As the intermediate portion 310 shifts from its straightened toward its curved configuration, the intermediate portion 310 travels along the outer surfaces of the bones rather than away from the outer surfaces of the bones as does the intermediate portion 20 of the bone plate 12 (see FIG. 23).

Figure 30:
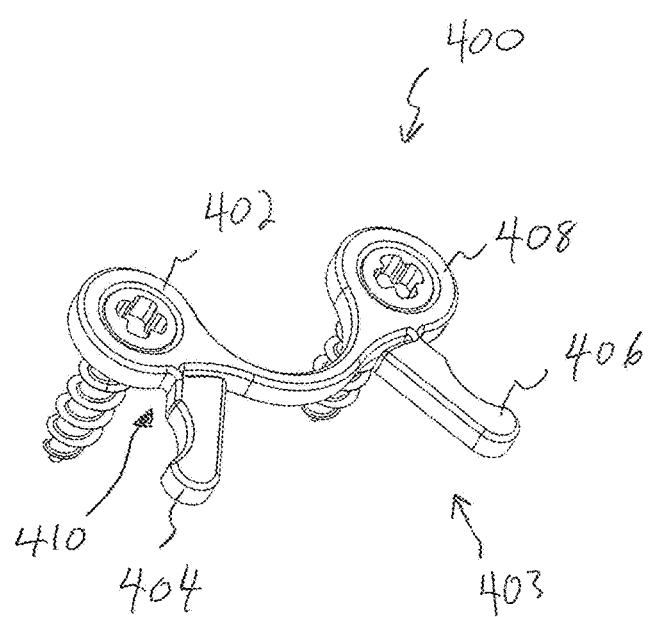
FIG. 30 is a perspective view of a bone compression device including a bone plate having integrated manipulators.

With reference to FIG. 30, a bone compression device 400 is provided having a bone plate 402 that is similar in many respects to the bone plate 302 as discussed above. However, the bone plate 402 has an integrated installation instrument 403 with manipulators 404, 406 that may be used to flex the bone plate 402 and then be removed from the bone plate 402 after installation of the bone plate 402 onto bones. In one form, the manipulators 404, 406 are integrally formed with a body 408 of the bone plate 402. As used herein, the term "integral" is intended to refer to being formed as one piece with another part.

Figure 31:
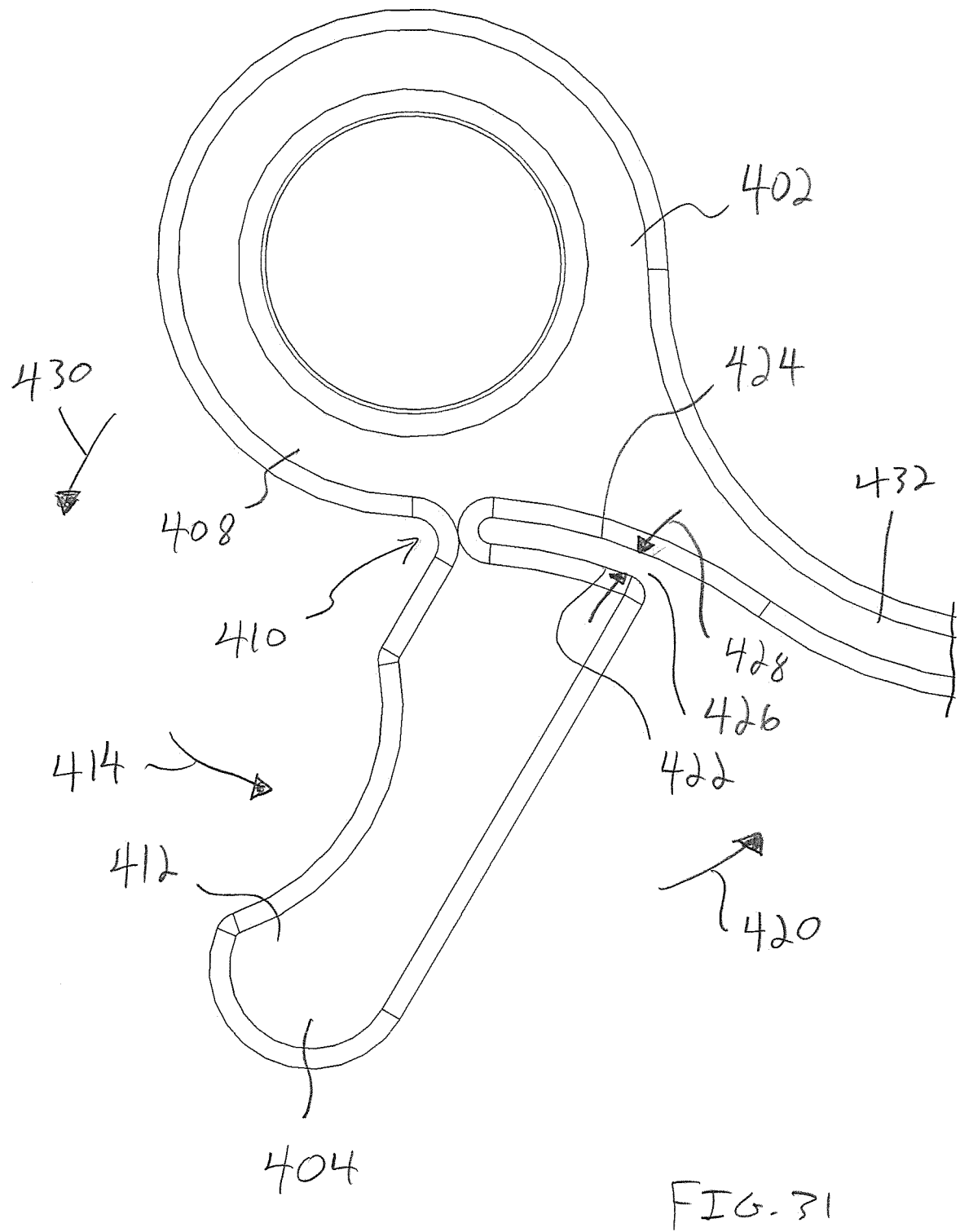
FIG. 31 is an enlarged, top plan view of the bone plate of FIG. 30 showing a connection between a body of the bone plate and the manipulator.

With reference to FIG. 31, the manipulator 404 is connected to the body 408 at a frangible portion 410. To deflect the bone plate 402 from an initial, unflexed configuration to a flexed, installation configuration, a user grasps handle portions 412 of the manipulators 404, 406 and squeezes the handle portions 412 together generally in direction 414. This pivots the manipulator 404 about the frangible portion 410 in direction 420 and brings a surface 422 of the manipulator 404 into contact with a surface 424 of the body 408. Stated differently, pivoting the manipulator 404 in direction 420 closes a gap 426 between the surfaces 422, 424 with a distance 428 between the surfaces 422, 424, decreasing as the manipulator 404 pivots in direction 420. With the surfaces 422, 424 abutting, continued squeezing of the handle portions 412 together moves the lobes 408 in directions 430 and straightens an intermediate portion 432. Once the bone plate 402 has been installed a user may bend, cut, or otherwise separate the manipulators 404, 406 from the bone plate body 408 at the frangible portions 410.

Figure 32:
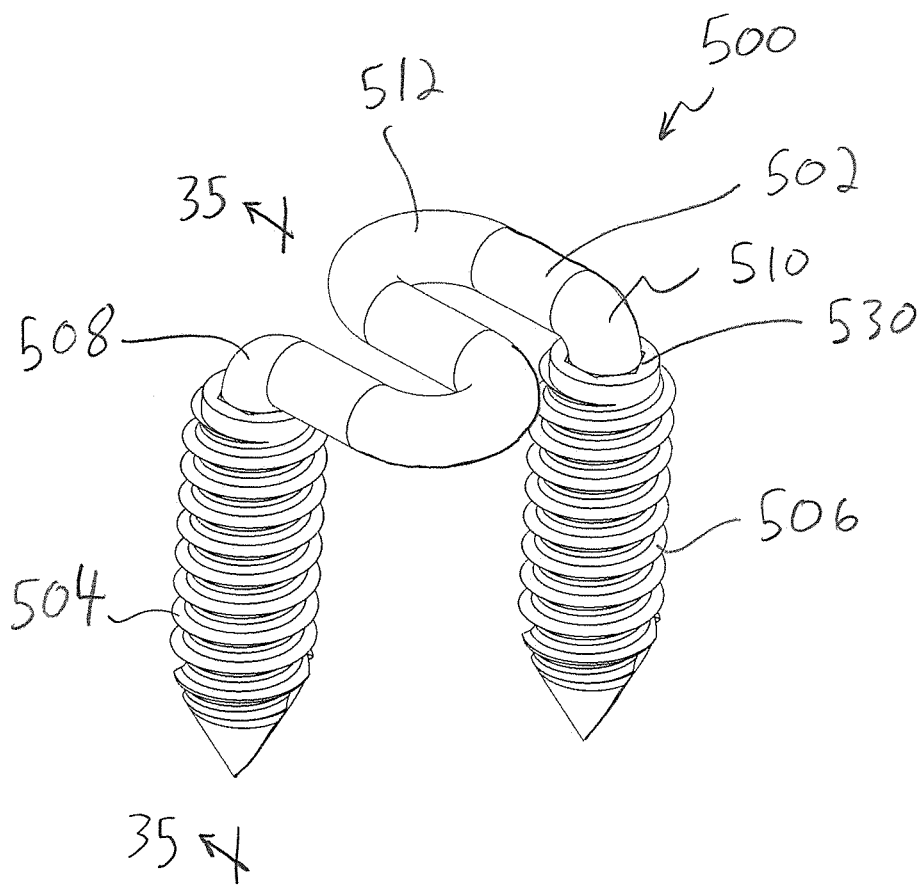
FIG. 32 is a perspective view of another bone compression device having a resilient body and bone screws.

With reference to FIGS. 32, and 33, a bone compression device 500 is provided having a resilient body 502 connecting bone screws 504, 506. The resilient body 502 includes end portions 508, 510 secured to the bone screws 504, 506 and an intermediate spring portion 512 configured to apply a compressive force to the bones connected to the bone screws 504, 506. The bone screws 504, 506 have blind bores 530 that receive the end portions 508, 510 of the resilient body 502. The bores 530 each have an upper portion with a hex drive configuration to accommodate a hex driver for driving the bone screws into 504, 506 into bone.

With reference to FIG. 33, a top plan view of the body 502 is provided showing the body 502 in an unflexed configuration. The body 502 has straight portions 516, 518, 520 and curved portions 522, 524 connecting the straight portions 516, 518, 520. To flex the body 502, the end portions 508, 510 are moved apart from each other in directions 521, 523. This causes the elbow portions 522, 524 to elastically flex to a more open configuration as shown in FIG. 34. Further, one or more of the straight portions 516, 518, 520 may elastically deform in the lengthwise direction.

To apply compression to bones, the bone screws 504, 506 are driven into the bones and the end portions 508, 510 of the body 502 are moved apart from each other to shift the body 502 to the flexed configuration thereof as shown in FIG. 34. The end portions 508, 510 are held in their spaced orientation to keep the body 502 flexed and the end portions 508, 510 are then advanced into the bores 530 of the bone screws 504, 506 previously driven into the bones. The resilient body 502 biases against the bone screws 504, 506 in directions 534, 536 as the body 502 returns toward its unflexed configuration and compresses the bones.

Figure 35:
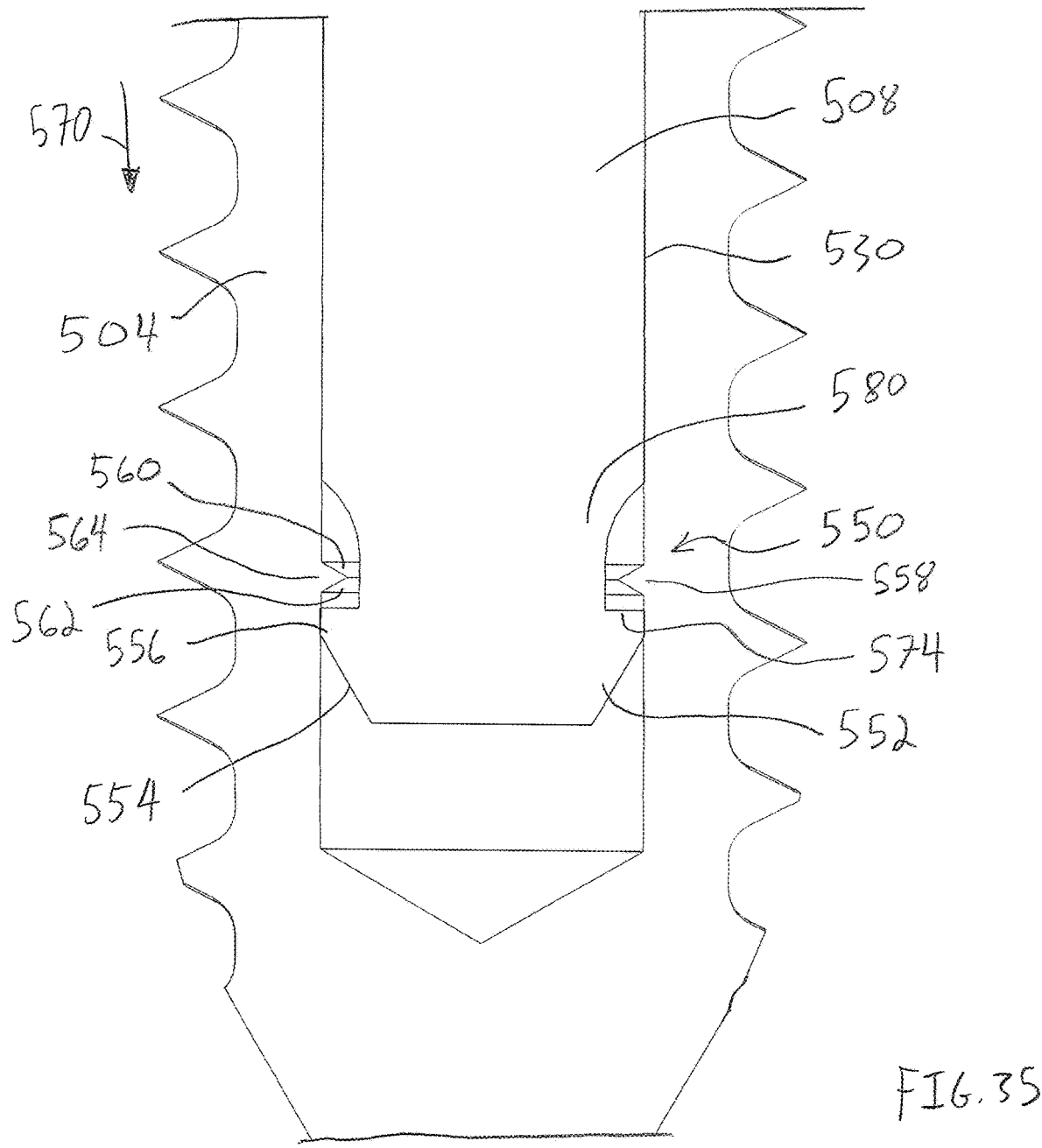
FIG. 35 is a cross-sectional view taken across line 35-35 in FIG. 32 showing a retention mechanism for keeping the end portion of the resilient body secured to the bone screw.

With reference to FIG. 35, the bone compression device 500 includes a retention mechanism 550 for maintaining the end portions 508, 510 in the bores 530 of the bone screws 504, 506. In one approach, the retention mechanism 550 includes a leading end portion 552 of the resilient body end portion 508. The leading end portion 552 has a cam surface 554 and an enlarged portion 556 that snaps past a retention portion 558 of the bone screw 504. More specifically, the retention portion 558 includes an annular collar 564 having an upper surface 560 and a lower surface 562. Advancing the leading end portion 552 in direction 570 into the bore 530 engages the cam surface 554 with the upper surface 560 of the collar 564. Continued advancing of the leading end portion 552 in direction 570 deflects the collar 564 and permits the enlarged portion 556 to snap past the collar 564. With the leading end portion 552 advanced past the collar 564, an upper surface 574 of the leading end portion 552 is arranged to abut the lower surface 562 of the retention portion 558 and resist back out of the leading end portion 552. In one approach, the leading end portion 508 has a smooth, volcano-shaped neck portion 580 spaced from the collar 564 with the leading end portion 552 captured in the bore 530 by the collar 564. The neck portion 580 permits the end portion 508 to turn within the bore 530 after installation of the bone compression device 500 which accommodates turning of the straight portion 520 in direction 582 (see FIG.

34) relative to the bone screw 504 as the resilient body 502 returns toward its unflexed configuration. The resilient body end portion 508 and bone screw 504 thereby form a pivot connection therebetween that permits reconfiguring of the resilient body 502 back toward its unflexed configuration while maintaining the end portion 508 securely connected to the bone screw 5034.

Figure 36:
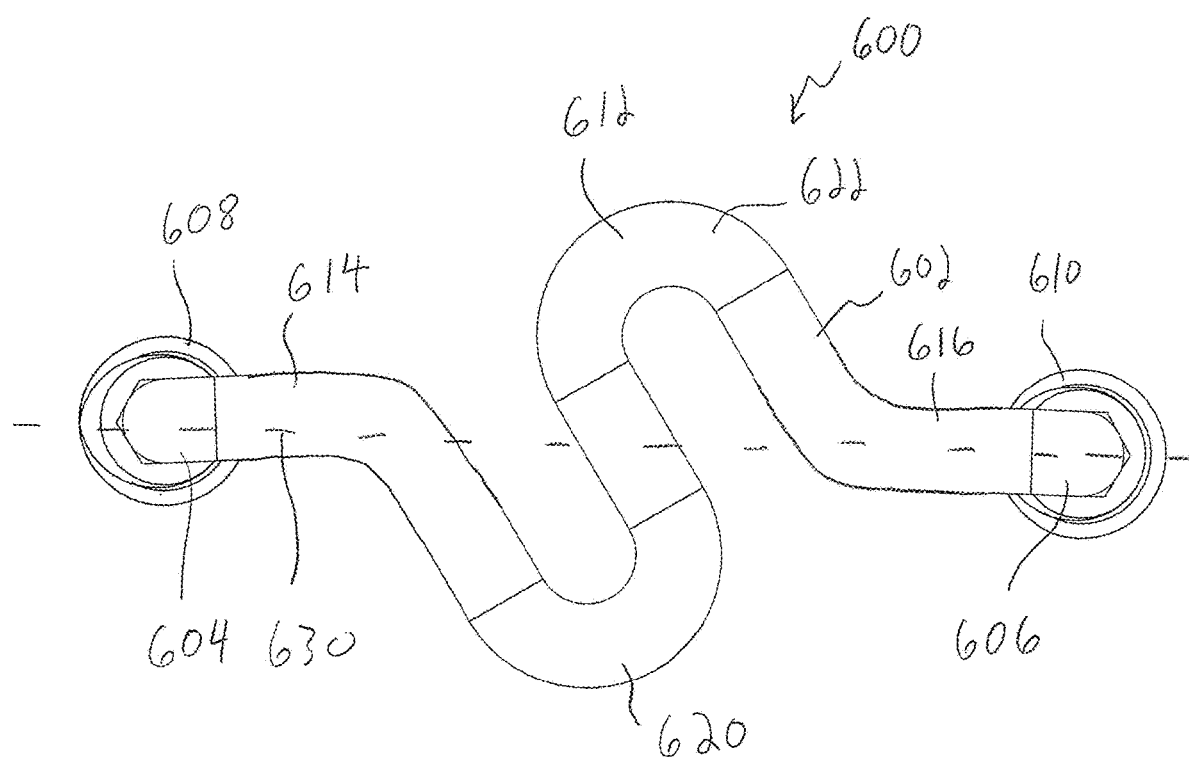
FIG. 36 is a top plan view of a bone compression device similar to the bone compression device of FIG. 32 showing straight legs of the resilient body connecting a spring portion of the body to end portions of the body.

With reference to FIG. 36, a bone compression device 600 is provided that is similar in many respects to the bone compression device 500. The bone compression device 600 includes a resilient body 602 having end portions 604, 606 that are configured to be secured to bone screws 608, 610 and a spring portion 612 intermediate the end portions 604, 606. One difference between the resilient body 602 and the resilient body 502 is that the resilient body 602 has straight legs 614, 616 connecting the end portions 604, 606, and the spring portion 612. The straight legs 614, 616 reduce turning of the end portions 604, 606 relative to the bone screws 608, 610 as the resilient body 602 returns toward its unflexed configuration. The straight legs 614, 616 reduce turning of the end portions 604, 606 relative to the bone screws 608, 610 because elbow portions 620, 622 of the spring portion 612 can flex and open as the resilient body 602 shifts toward its flexed configuration while the straight legs 614, 616 remain generally aligned along an axis 630. The bone compression device 600 may have retention mechanisms that rigidly fix the resilient body 602 to the bone screws 608, 610 since the end portions 608, 610 generally do not turn relative to the bone screws 608, 610 as the resilient body 602 returns toward its unflexed configuration.

The bone compression devices discussed above may be used in a variety of applications, such as hand and foot bone fragment and osteotomy fixation and joint arthrodesis, fixation of proximal tibial metaphysis osteotomy, and adjunctive fixation of small bone fragments. The bone compression devices may be used with bones such as the femur, humerus, clavicle, sternum, ribs, and pelvis.

Those skilled in the art will recognize that a wide variety of modifications, alterations, and combinations can be made with respect to the above-described embodiments without departing from the spirit and scope of the invention, and that much modifications, alterations, and combinations are to be viewed as being within the ambit of the inventive concept.

What is claimed is:

1. A bone plate system comprising:
   a plurality of bone screws;
   a resilient bone plate having a unitary, one-piece construction;
   lobes of the bone plate having through openings to receive the bone screws, each of the through openings having an inner diameter;
   lower surface portions of the lobes to be positioned adjacent bones and upper surface portions of the lobes opposite the lower surface portions;
   a single elongate intermediate portion of the bone plate connecting the lobes, the intermediate portion having a length extending between the lobes;
   the intermediate portion having an upper surface portion, a lower surface portion, and a thickness extending between the upper and lower surface portions perpendicular to the length, the thickness of the intermediate portion being less than the length thereof;
   the intermediate portion having a width perpendicular to the length and the thickness, the width of the intermediate portion being less than the length of the intermediate portion and less than the inner diameter of at least one of the through openings of the lobes;
   the bone plate having an unflexed configuration wherein the intermediate portion is bent upwardly and the lobes are closer together and a flexed configuration wherein the intermediate portion is straightened and the lobes are farther apart;
   wherein the lobes extend transversely to one another with the bone plate in the unflexed configuration and the lobes are coplanar with one another with the bone plate in the flexed configuration; and
   instrument receiving portions of the lobes to connect to an instrument that maintains the bone plate in the flexed configuration for positioning of the bone plate adjacent the bones.

2. The bone plate system of claim 1 wherein the lobes include inner portions defining the through openings and peripheral portions outward of the through openings that include the instrument receiving portions of the lobes.

3. The bone plate system of claim 1 wherein the lobes include annular walls and the instrument receiving portions of the lobes are radially outward of the through openings of the through openings.

4. The bone plate system of claim 1 wherein the lobes are enlarged ends of the bone plate.

5. The bone plate system of claim 1 wherein the instrument receiving portions of the lobes include lips.

6. The bone plate system of claim 1 wherein the instrument receiving portions of the lobes include:
   lips; and
   notches below the lips to receive portions of the instrument.

7. The bone plate system of claim 1 wherein the instrument receiving portions each include a lip and a depending flat.

8. The bone plate system of claim 1 wherein the upper and lower surface portions of the lobes extend about the through openings and the lobes include arcuate side surfaces extending intermediate the upper and lower surface portions.

9. The bone plate system of claim 1 wherein each lobe includes arcuate side surfaces extending between the upper and lower surface portions of the lobe and a flat connecting the arcuate side surfaces.

10. The bone plate system of claim 1 wherein the through openings extend between the upper and lower surface portions of the lobes along central axes of the through openings; and
    wherein the central axes of the through openings extend transverse to one another with the bone plate in the unflexed configuration and extend parallel to one another with the bone plate in the flexed configuration.

11. The bone plate system of claim 1 wherein the intermediate portion is coplanar with the lobes with the bone plate in the flexed configuration.

12. The bone plate system of claim 1 wherein the lobes and the intermediate portion are coplanar with the bone plate in the flexed configuration and the intermediate portion is bent upward out of the plane and the lobes extend transversely relative to one another with the bone plate in the unflexed configuration.

13. The bone plate system of claim 1 wherein the intermediate portion includes a pair of portions extending at a first angle relative to one another with the bone plate in the unflexed configuration and at a second angle relative to one another with the bone plate in the flexed configuration, the second angle being larger than the first angle.

14. The bone plate system of claim 1 wherein the intermediate portion has a center bottom surface portion, the center bottom surface portion being below the upper surface portions of the lobes with the bone plate in the flexed configuration and above the upper surface portions of the lobes with the bone plate in the unflexed configuration.

15. The bone plate system of claim 14 wherein the center bottom surface portion of the intermediate portion is coplanar with the lower surface portions of the lobes with the bone plate in the flexed configuration.

16. The bone plate system of claim 14 wherein the intermediate portion has a center upper surface portion, the center upper surface portion having a first position above the upper surface portions with the bone plate in the unflexed configuration and a second position below the first position with the bone plate in the flexed configuration.

17. The bone plate system of claim 1 wherein the intermediate portion is straight with the bone plate in the flexed configuration.

18. The bone plate system of claim 1 wherein the lobes include annular walls and the intermediate portion extends radially from the annular walls.

19. The bone plate system of claim 1 wherein the bone plate includes nitinol.

20. The bone plate system of claim 1 wherein the bone plate is of a shape memory material that causes the bone plate to change from the flexed configuration to the unflexed configuration in response to an internal temperature of a patient.

21. The bone plate system of claim 1 wherein the instrument receiving portions of the lobes are configured to form non-rotatable connections with the instrument.

22. The bone plate system of claim 1 wherein the bone screws each include a head portion including threads and a shank portion configured to be driven into one of the through openings of the lobes; and
wherein the lobes include threads of the through openings to engage the threads of the bone screws and resist back-out of the bone screws.

23. The bone plate system of claim 1 wherein the bone plate has only two through openings to receive the bone screws.

24. The bone plate system of claim 1 wherein the bone plate is of a superelastic nitinol.

25. The bone plate system of claim 1 wherein the instrument receiving portions each include:
a lip; and
a notch below the lip to receive a portion of the instrument;
wherein each lobe of the bone plate includes:
a pair of arcuate side surface portions extending between the upper and lower surface portions of the lobe for being received in the instrument; and
a flat depending from the lip and connecting the pair of arcuate side portions, the flat configured to engage a flat surface of the portion of the instrument and inhibit turning of the lobe relative to the instrument.

* * * * *